(12) United States Patent
Malandain et al.

(10) Patent No.: US 8,187,305 B2
(45) Date of Patent: May 29, 2012

(54) METHODS AND APPARATUS FOR DEPLOYING SPINOUS PROCESS CONSTRAINTS

(75) Inventors: Hugues Malandain, Mountain View, CA (US); Todd Alamin, Woodside, CA (US); Manish Kothari, San Rafael, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 220 days.

(21) Appl. No.: 12/478,953

(22) Filed: Jun. 5, 2009

(65) Prior Publication Data

US 2010/0004701 A1 Jan. 7, 2010

Related U.S. Application Data

(60) Provisional application No. 61/059,530, filed on Jun. 6, 2008.

(51) Int. Cl.
*A61B 17/70* (2006.01)
(52) U.S. Cl. ...................... 606/248; 606/86 A
(58) Field of Classification Search ................ 606/86 A, 606/99, 246–249
See application file for complete search history.

(56) References Cited

U.S. PATENT DOCUMENTS

| | | | |
|---|---|---|---|
| 3,648,691 A | 3/1972 | Lumb et al. | |
| 4,246,660 A | 1/1981 | Wevers | |
| 4,643,178 A | 2/1987 | Nastari et al. | |
| 4,708,132 A | 11/1987 | Silvestrini | |
| 4,743,260 A | 5/1988 | Burton | |
| 4,772,286 A | 9/1988 | Goble et al. | |
| 4,776,851 A | 10/1988 | Bruchman et al. | |
| 4,794,916 A | 1/1989 | Porterfield et al. | |
| 4,870,957 A | 10/1989 | Goble et al. | |
| 4,955,910 A | 9/1990 | Bolesky | |
| 4,966,600 A | 10/1990 | Songer et al. | |
| 5,002,574 A | 3/1991 | May et al. | |
| 5,011,484 A | 4/1991 | Breard | |
| 5,011,494 A | 4/1991 | von Recum et al. | |
| 5,092,866 A | 3/1992 | Breard et al. | |
| 5,108,433 A | 4/1992 | May et al. | |
| 5,116,340 A | 5/1992 | Songer et al. | |
| 5,171,280 A | 12/1992 | Baumgartner | |

(Continued)

FOREIGN PATENT DOCUMENTS

EP 0 322 334 A1 6/1989

(Continued)

OTHER PUBLICATIONS

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

(Continued)

*Primary Examiner* — Thomas J Sweet
*Assistant Examiner* — Megan Wolf
(74) *Attorney, Agent, or Firm* — Wilson Sonsini Goodrich & Rosati

(57) ABSTRACT

A surgical tool for deploying an implant includes an elongate outer shaft having a proximal end, a distal end and a central channel therebetween. An elongate inner shaft is at least partially slidably received in the central channel and an actuator mechanism is operatively coupled with either the outer or inner shaft. The tool also includes a piercing element that is coupled with the outer shaft and releasably coupled with the implant.

95 Claims, 40 Drawing Sheets

U.S. PATENT DOCUMENTS

| | | |
|---|---|---|
| 5,180,393 A | 1/1993 | Commarmond |
| 5,282,863 A | 2/1994 | Burton |
| 5,354,303 A | 10/1994 | Spaeth et al. |
| 5,395,374 A | 3/1995 | Miller et al. |
| 5,415,658 A | 5/1995 | Killpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,609,634 A | 3/1997 | Voydeville |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A | 3/1998 | Bevan et al. |
| 5,902,305 A | 5/1999 | Beger et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,899,716 B2 | 5/2005 | Cragg et al. |
| 7,029,475 B2 | 4/2006 | Panjabi |
| 7,163,558 B2 | 1/2007 | Senegas et al. |
| 7,201,751 B2 | 4/2007 | Zucherman et al. |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,591,837 B2 | 9/2009 | Goldsmith |
| 2002/0068948 A1* | 6/2002 | Stormby et al. .............. 606/151 |
| 2002/0095154 A1 | 7/2002 | Atkinson et al. |
| 2002/0147449 A1 | 10/2002 | Yun |
| 2002/0151978 A1 | 10/2002 | Zacouto et al. |
| 2003/0088251 A1 | 5/2003 | Braun et al. |
| 2004/0010270 A1* | 1/2004 | Wells .......................... 606/139 |
| 2004/0024458 A1 | 2/2004 | Senegas et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0215341 A1 | 10/2004 | Sybert et al. |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 | 6/2005 | Molz, IV et al. |
| 2005/0154390 A1 | 7/2005 | Biedermann et al. |
| 2005/0192581 A1 | 9/2005 | Molz et al. |
| 2005/0267470 A1 | 12/2005 | McBride |
| 2006/0036324 A1 | 2/2006 | Sachs et al. |
| 2006/0041259 A1 | 2/2006 | Paul et al. |
| 2006/0052800 A1* | 3/2006 | Greenhalgh .................. 606/139 |
| 2006/0064166 A1 | 3/2006 | Zucherman et al. |
| 2006/0069447 A1 | 3/2006 | Disilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 | 10/2008 | Bennett et al. |
| 2008/0281423 A1 | 11/2008 | Sheffer et al. |
| 2008/0312693 A1 | 12/2008 | Trautwein et al. |
| 2008/0319487 A1 | 12/2008 | Fielding et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |
| 2009/0264932 A1 | 10/2009 | Alamin et al. |
| 2009/0270918 A1 | 10/2009 | Attia et al. |
| 2010/0023060 A1 | 1/2010 | Bennett et al. |
| 2010/0036424 A1 | 2/2010 | Fielding et al. |
| 2010/0234890 A1 | 9/2010 | Alamin et al. |
| 2010/0234894 A1 | 9/2010 | Alamin et al. |
| 2010/0249839 A1 | 9/2010 | Alamin et al. |

FOREIGN PATENT DOCUMENTS

| | | |
|---|---|---|
| EP | 0 743 045 A2 | 11/1996 |
| EP | 0743045 A3 | 12/1996 |
| EP | 1 994 901 A1 | 11/2008 |
| FR | 2 681 525 A1 | 3/1993 |
| FR | 2 714 591 | 7/1995 |
| FR | 2 717 675 A1 | 9/1995 |
| FR | 2 828 398 A1 | 2/2003 |
| FR | 2 851 154 | 8/2004 |

| | | |
|---|---|---|
| FR | 2 884 136 A1 | 10/2006 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 1/2004 |
| WO | WO 2004/052246 | 6/2004 |
| WO | WO 2004/073532 | 9/2004 |
| WO | WO 2004/073533 | 9/2004 |
| WO | WO 2005/110258 A1 | 11/2005 |
| WO | WO 2008/039460 A2 | 4/2008 |
| WO | WO 2008/051801 | 5/2008 |
| WO | WO 2008/051802 | 5/2008 |
| WO | WO 2008/051802 A3 | 7/2008 |
| WO | WO 2008/039460 A3 | 8/2008 |
| WO | WO 2008/051801 A3 | 8/2008 |

OTHER PUBLICATIONS

Abbott Spine, Wallis Surgical Technique [Product Brochure], 2006; 24 pages total.

Al Baz et al., "Modified Technique of Tension Band Wiring in Flexion Injuries of the Middle and Lower Cervical Spine," Spine, 1995; 20(11): 1241-1244.

Dickman et al., "Comparative Mechanical Properties of Spinal Cable and Wire Fixation Systems," Spine, Mar. 15, 1997; 22(6): 596-604.

Frymoyer et al., "An Overview of the Incidence and Costs of Low Back Pain" Orthop. Clin. North Am., 1991;22: 263-271.

Garner et al., "Development and Preclinical Testing of a New Tension-Band Device for the Spine: the Loop system," European Spine Journal, 2002; 11 (Suppl 2): S186-191.

Heller, "Stability of Different Wiring Techniques in Segmental Spinal Instrumentation. An Experimental Study," Archives of Orthopedic and Trauma Surgery, Nov. 1997; 117(1-2): 96-99.

Leahy et al., "Design of Spinous Process Hooks for Flexible Fixation of the Lumbar Spine," Proceedings of the Institution of Mechanical Engineers, Part H, Journal of Engineering in Medicine, Sep. 2000; 214( 5):479-487.

Leahy et al., "Mechanical Testing of a Flexible Fixation Device for the Lumbar Spine," Proceedings of the Institution of Mechanical Engineers, Part H: Journal of Engineering in Medicine, Sep. 27, 2000; 214(5): 489-495.

Medtronic Sofamor Danek USA, Inc., Diam™ System Implant; 2006 [Product Brochure]; downloaded from the Internet: <http://spineinfo.ru/~files/DIAMST.pdf>, 20 pages total.

Minns et al., "Preliminary Design and Experimental Studies of a Novel Soft Implant for Correcting Sagittal Plane Instability in the Lumbar Spine," Spine, Aug. 15, 1997; 22(16): 1819-1825.

Miyasaka et al., "Radiographic Analysis of Lumbar Motion in Relation to Lumbosacral Stability: Investigation of Moderate and Maximum Motion," Spine, Mar. 15, 2000; 25(6): 732-737.

Papp et al., "An in Vitro Study of the Biomechanical Effects of Flexible Stabilization on the Lumbar Spine," Spine, Jan. 15, 1997, 22(2): 151-155.

Shepherd et al., "Spinous Process Strength," Spine, Feb. 1, 2000; 25(3): 319-323.

Shepherd, "Slippage of a Spinous Process Hook During Flexion in a Flexible Fixation System for the Lumbar Spine," Medical Engineering and Physics, Mar. 2001; 23(2): 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

International Search Report and Written Opinion of PCT Application No. PCT/US2009/046484, mailed Jul. 28, 2009, 13 pages total.

* cited by examiner

METHODS AND APPARATUS FOR DEPLOYING SPINOUS PROCESS CONSTRAINTS

CROSS-REFERENCES TO RELATED APPLICATIONS

The present application is a non-provisional of, and claims the benefit of priority under 35 U.S.C. §119(e) of U.S. Provisional Application No. 61/059,530 filed Jun. 6, 2008, the entire contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention relates generally to methods and tools for deploying a device through a barrier. More particularly, the present invention relates to methods and tools for deploying spinous process constraint devices through tissue in patients having back pain or other spinal conditions.

The human spine structure includes four curves that generally form an "S" shape. One of these curves, lumbar lordosis, results in an intervertebral space that is larger in the front (anterior) than back (posterior). Unfortunately, a backward shift in the intervertebral disc in this lower back region is particularly susceptible to pain generation since the nerve roots and dura matter emerge at the posterior aspect of the vertebral column. The evolutional change to an upright position has not included concomitant anatomical adaption. Thus, the human spine has an anatomy that more readily withstands extension (i.e. standing or arching backwards) rather than flexion (i.e. sitting or bending forward) and can quickly destabilize during certain movements.

Spinal stability is highly dependent on the patency of attached soft tissue such as ligaments, spinal load and posture as well as task requirements. In particular, the ligaments and disc play a key role in keeping each spine segment stable and aligned. Degeneration of ligaments, disc or other tissue structures can lead to inability of the spine segment to maintain stability even over a normal range of loads. Instability of the lumbar spine has been suggested to be both a cause and a consequence of acute, recurring or chronic low back pain. It is estimated that 80% of the general population will suffer from backache or lumbago during their lifetime (Fryomoyer et al., "An Overview of the Incidence and Costs of Low Back Pain" *Orthrop. Clin. North Am.* (1991) 22:263-271).

A major source of chronic low back pain is discogenic pain, also known as internal disc disruption. Patients suffering from discogenic pain tend to be young, otherwise healthy individuals who present with pain localized to the back. Discogenic pain usually occurs in the lower back at the discs located at the L4-L5 or L5-S1 junctions of the lumbar spine. Pain tends to be exacerbated when patients put their spines into flexion and relieved when they put their lumbar spines into extension. Flexion and extension are known to change the mechanical loading pattern of a lumbar segment. During extension, the axial loads borne by this segment are shared by the disc and the facet joints. It is estimated that about 30% of the load is borne by the facet joints. In flexion, however, the segmental load is borne almost entirely by the disc. Furthermore, when the segment is in flexion, the nucleus shifts posteriorly, changing the loads on the posterior portion of the annulus (which is innervated), likely causing its fibers to be subject to tension and shear forces. Segmental flexion, then, both increases the loads borne by the disc and causes them to be borne in a more painful way. Discogenic pain can be severely disabling. For some patients, it can deleteriously affect their ability to work, recreate and otherwise enjoy their lives.

Pain experienced by patients with discogenic low back pain can be thought of as flexion instability, and is related to flexion instability manifested in other conditions. The most prevalent of these is spondylolisthesis, a spinal condition in which abnormal segmental translation is exacerbated by segmental flexion. This condition is characterized by a forward slipping (i.e. anterior displacement) of one or more vertebrae that invariably results in stenosis of the spinal canal. Slippage can occur if the adjacent ligatures are weak, which is often the case in the lumbar area, particularly if people live a sedentary life style. The tools described herein may be used to help deploy spinal implants that treat these and other spinal disorders associated with segmental flexion for which the prevention or control of spinal segmental flexion is desired.

Patients with discogenic pain accommodate their syndrome by avoiding positions such as sitting, which cause their painful segment to go into flexion, and preferring positions such as standing, which maintain their painful segment in extension. One approach to reducing discogenic pain involves the use of a lumbar support often seen in office chairs. Biomechanically, the attempted effect of the ubiquitous lumbar support is also to maintain the painful lumbar segment in the less painful extension position.

Current treatment alternatives for patients diagnosed with back pain are limited. At one end of the treatment continuum, a patient may elect to follow a conservative path, such as physical therapy, massage, anti-inflammatory and analgesic medications, muscle relaxants, and/or epidural steroid injections. This is usually the first treatment option because it is simple and least invasive. However, most of these patients continue to suffer with a significant degree of pain.

At the opposite end of the treatment spectrum, a patient may elect to undergo invasive and risky surgeries including spinal fusion. Fusion often requires discectomy (i.e. removal of the disk) together with fusion of adjacent vertebra. This procedure may or may not also include instrumentation of the affected spinal segment including, for example, pedicle screws and stabilization rods. Fusion is not usually recommended for discogenic pain because it is irreversible, costly, associated with high morbidity, and of questionable effectiveness. It can lead to long term complications and suffering for the patient, often out of proportion to the original condition. The use of metal rods, screws and plates represent a rather crude approach to the treatment of discogenic pain. Despite its drawbacks, however, spinal fusion for discogenic pain remains common due to the lack of viable alternatives.

An alternative method that is not commonly used in practice but has been approved for use by the United States Food and Drug Administration (FDA), is the application of bone cerclage devices that can encircle the spinous processes or other vertebral elements and thereby create a restraint to motion. Physicians typically apply a tension or elongation to the devices that apply a constant and high force on the anatomy, thereby fixing the segment in one position and allowing effectively no motion. The lack of motion allowed after the application of such devices is thought useful to improve the likelihood of fusion performed concomitantly; if the fusion does not take, these devices can fail through breakage of the device or of the spinous process to which the device is attached. These devices are designed for static applications and are not designed to allow for a dynamic elastic resistance to flexion across a range of motion. The purpose of bone cerclage devices and the other techniques described above is to almost completely restrict measurable motion of the vertebral segment of interest. This loss of motion at a given segment gives rise to abnormal loading and motion at adjacent segments leading eventually to adjacent segment morbidity and other related problems.

The desperate need for better treatment options has lead to the introduction of a growing number of interspinous process devices. Designs vary from static spacers to dynamized devices. Furthermore, they are composed of a range of different materials including bone allograft, titanium, polyetheretherketone, and elastomeric compounds. The common link between them is the mechanical goal of distracting the spinous processes to affect the intervertebral relationship.

Recently, a minimally invasive and potentially more effective treatment for discogenic pain has been developed which offers a welcome alternative to the aforementioned conservative and invasive treatment extremes. A spinal implant (i.e. spinous process constraint) has been designed which inhibits spinal flexion while allowing substantially unrestricted spinal extension. Additional disclosure is provided in U.S. Patent Publication No. 2005/0216017A1 (now U.S. Pat. No. 7,458,981), the entire contents of which are incorporated herein by reference. Generally, the spinous process constraint is implanted with one or more tools that facilitate the procedure for a surgeon.

The successful placement of this innovative spinous process constraint is determined, in large part, by the way in which it is positioned in the patient. Additionally, during surgical implantation of a spinous process constraint, blood and tissue may make it difficult for a surgeon to see the implant. Accordingly, specific tools have been developed to make implant positioning and deployment faster, easier, less invasive, more accurate and more precise.

For the forgoing reasons, there is a need to provide methods and tools that facilitate deployment of spinous process constraints as well as other implants. As such, the following invention relates to methods and instruments for use in positioning and deploying a spinous process constraint like the implant described in U.S. Patent Publication No. 2005/0216017A1 (now U.S. Pat. No. 7,458,981).

2. Description of the Background Art

U.S. Patent Publication No. 2005/0216017A1 is described in greater detail below. Other patents and published applications that address problems associated with spinal stability include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. 2002/0151978; 2004/0024458; 2004/0106995; 2004/0116927; 2004/0117017; 2004/0127989; 2004/0172132; 2005/0033435; 2005/0049708; 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1. However, each of these references suffers from one or more of the disadvantages previously described.

BRIEF SUMMARY OF THE INVENTION

The present invention provides surgical methods and tools. More particularly, the tools and methods relate to deployment of spinal implants such as spinous process constraints in the treatment of discogenic pain and other conditions, such as degenerative spondylolisthesis. These tools and methods provide a surgeon a less invasive and more reliable way of deploying spinal implants.

In a first aspect of the present invention, a surgical tool for deploying an implant comprises an elongate outer shaft having a proximal end, a distal end and a central channel therebetween. The tool also comprises an elongate inner shaft that is at least partially slidably received in the central channel and an actuator mechanism that is operatively coupled with either the outer or inner shaft. A leader having a piercing element such as a needle is releasably coupled with the inner shaft or the outer shaft or both shafts and the leader may also be coupled with the implant. The leader is adapted to be passed through tissue which may comprise an interspinous ligament disposed between adjacent spinous processes.

The actuator mechanism may comprises a rotatable knob as well as an indicator for indicating the position of the outer shaft relative to the inner shaft. The indicator may provide audible, tactile or visual feedback to an operator.

The outer shaft may comprise an aperture disposed near the outer shaft's distal end and the inner shaft may also comprise an aperture near it's distal end. The outer shaft aperture is at least partially aligned with the inner shaft aperture so as to permit the leader to be slidably received in both apertures. The outer shaft may also have a keying feature that only permits locking of the outer shaft with the leader when the leader is in a predetermined orientation relative to the outer shaft. The keying feature may comprise a channel near the outer shaft's distal end that has a first opening and a second opening opposite the first, with the first opening being larger than the second opening.

The tool may further comprise a handle that is coupled with the outer shaft near its proximal end. Sometimes the handle may comprise a pistol grip and the handle may be oriented along an axis that is substantially parallel to a longitudinal axis in which the leader lies. The leader may include a piercing element such as a needle as well as a coupling mechanism for releasably holding the implant. The coupling mechanism may be a lasso or a closeable loop with an optional movable collar. The coupling mechanism may comprise a filament having loops on both ends of the filament. The filament may be slidably threaded through the leader and the filament may have first and second ends that are knotted together to form a closed loop. The filament may be radiopaque. In some embodiments, the implant is separated from the leader by severing. The leader may have a sharp piercing tip and a flat or flared shoulder adapted to distend an initial puncture created by the sharp piercing tip.

In another aspect of the present invention, a surgical system for deploying an implant comprises an elongate outer shaft having a proximal end, a distal end and a central channel therebetween. An elongate inner shaft is at least partially slidably received in the central channel and an actuator mechanism is operatively coupled with either the outer or inner shaft. A leader having a piercing element is releasably coupled with the inner and/or outer shaft and the implant. The system also includes a capture arm having a capture mechanism for releasably capturing the leader. The leader is adapted to pass through tissue such as an interspinous ligament disposed between two adjacent spinous processes.

The capture mechanism may comprises an aperture near a distal end of the capture arm. Also, the capture mechanism may include a guard that obstructs at least a portion of the leader after capture thereof so as to prevent exposure of sharp portions of the leader. The system may further include a handle that is coupled with the outer shaft near its distal end.

In still another aspect of the present invention, a surgical method for deploying an implant comprises piercing tissue with a leader coupled to a tool shaft and actuating an actuator on the tool shaft to allow release of the leader from the shaft. The method also includes coupling the leader with the implant and advancing the leader and implant through the tissue. Additional steps in the method include releasing the leader from the implant and removing the leader from a patient's body, the implant remaining therein.

In some embodiments of the method, piercing may comprise orienting the leader relative to the tissue using an indicator on the tool shaft. Piercing may create an initial puncture and the method may also include distending the tissue to enlarge the puncture. In any of the aspects of the present invention, the implant may comprise a spinous process constraint and the tissue may include an interspinous ligament disposed between adjacent spinous processes.

Actuating the actuator may comprise rotating a knob. An inner shaft may be disposed at least partially in the tool shaft and actuating the actuator may comprise linearly moving the tool shaft relative to the inner shaft. Releasing the leader may also comprise actuating an actuator on the tool shaft. When an inner shaft is disposed at least partially in the tool shaft, releasing the leader may comprise aligning an aperture in the inner shaft with an aperture in the tool shaft. The releasing step may also include linearly moving the tool shaft relative to the inner shaft, or slidably disengaging the leader from the tool.

Sometimes coupling the leader comprises closing a lasso around the implant or in other embodiments, the leader may comprise a loop and coupling the leader may comprise advancing a collar over the loop so as to capture the implant with the loop. Coupling the leader may also comprise hooking the implant with a loop.

Sometimes the leader may comprise a filament and advancing the leader comprises pulling the filament through the tissue. The filament may be radiopaque. Advancing the leader may also comprise capturing the leader with a capture tool and capturing the leader may comprise covering the leader with a guard to prevent exposure of sharp portions of the leader.

The method may further comprise releasably locking the leader with the shaft, for example, by actuating an actuator mechanism on the shaft. Other embodiments may further comprise tactilely distinguishing the leader from the tissue or adjacent tissue with an operator's hand and the leader may be shaped to pass preferentially through tissue in one direction. The step of advancing the leader and implant through tissue may comprise folding the implant around a portion of the leader, loop or lasso such that the folded portion forms a leading edge and the leading edge is advanced through the tissue. Thus, a free end of the implant trails the leading edge and is protected from damage as the implant is passed through the tissue. Radiopaque markers on the implant may be observed with fluoroscopy in order to verify the position of the implant in the patient. Other components may also be radiopaque. For example, the leader, the loop or the lasso may visible under a fluoroscope. These components may be fabricated from radiopaque materials or radiopaque markers may be attached to them enhance radiopacity.

In another aspect of the present invention, a surgical system comprises a spinous process constraint device having a tether structure and a compliance member, the tether structure adapted to be coupled to adjacent spinous processes or a spinous process and a sacrum, wherein the spinous process constraint device provides a force resistant to flexion of a spinal segment. The system also includes a leader coupled with the spinous process constraint device. The leader has a distal piercing tip adapted to pass through tissue without resulting in trauma to adjacent tissue, wherein the tissue is disposed either between the two adjacent spinous processes, or between the spinous process and the sacrum, or the tissue comprises the spinous process or the sacrum. The piercing tip is adapted to be distinguished from the tissue and the adjacent tissue by tactile sensation and may also be adapted to create an aperture in the tissue with the aperture sized to receive the tether structure. The piercing tip may be shaped to preferentially pierce the tissue in a single direction. The piercing tip may also comprise a tapered shoulder region adapted to expand the channel as the piercing tip passes therethrough. The leader may comprise a woven textile tube having a an open end and a rigid tip. The open end may be sized to receive a portion of the tether structure. The rigid tip may also comprise a tapered shoulder region that is adapted to expand the channel as the piercing tip is passed therethrough. The system may also include a handle detachable from the leader and a keyway element disposed on the handle or the leader that is adapted to permit coupling of the leader with the handle in a single orientation.

In still another aspect of the present invention, a surgical method for advancing an implant through tissue comprises providing an implantable strap having a free end and a woven textile tube having an open end and a tipped end. The free end of the strap is advanced into the open end of the textile tube and the tipped end is passed through the tissue. The textile tube is advanced through the tissue and the textile tube collapses over the strap as the textile tube is advanced through the tissue. Thus, the strap is held in the textile tube as the textile tube is advanced through the tissue so that the strap may be advanced through the tissue and then the strap is released from the textile tube. The tipped end may comprise a metal tip and the tissue may comprise an interspinous ligament disposed between adjacent spinous processes or a spinous process, or the sacrum.

These and other embodiments are described in further detail in the following description related to the appended drawing figures.

DETAILED DESCRIPTION OF THE INVENTION

The following exemplary embodiments of tools will be described in the context of applying a constraint around or through the spinous processes. This is intended to be for illustrative purposes only and one of ordinary skill in the art will recognize that the tools disclosed herein may be used in a number of other applications and therefore are not limited to spinal surgery.

Figure 1A:
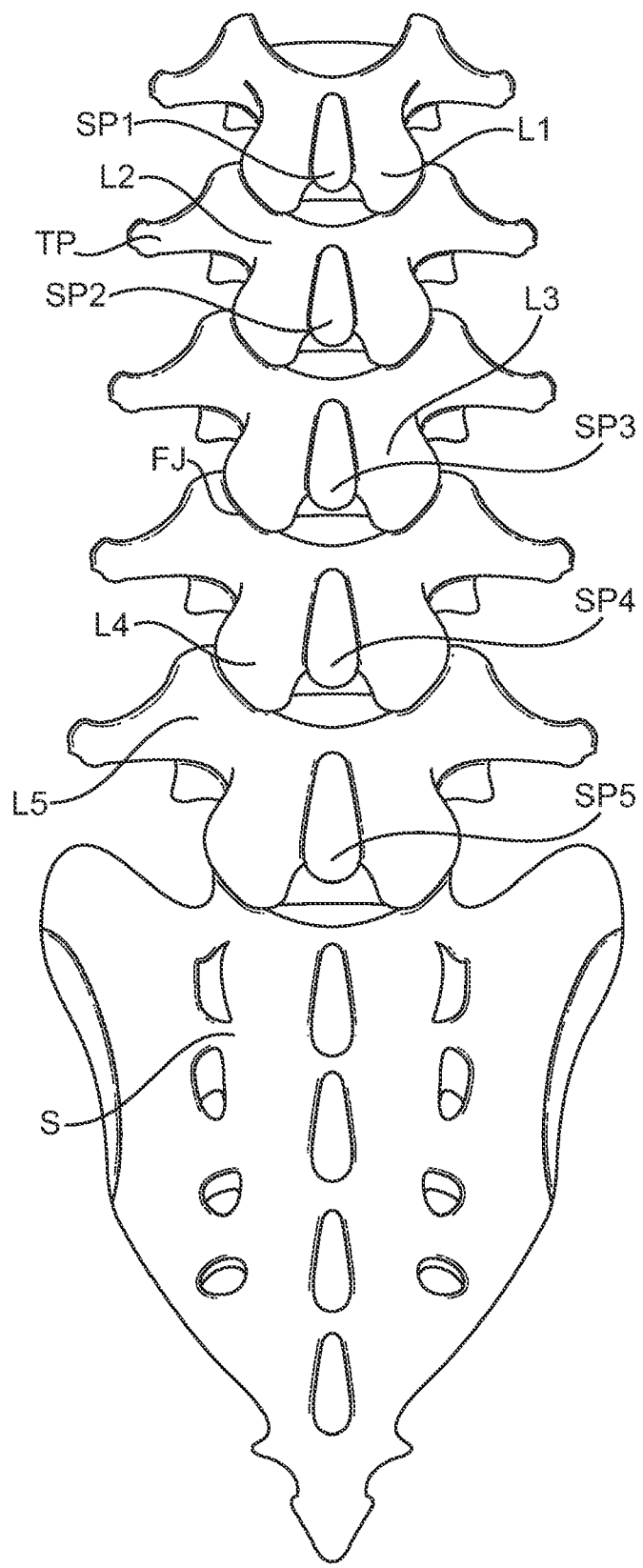
FIG. 1A is a schematic diagram illustrating the lumbar region of the spine.
Figure 1B:
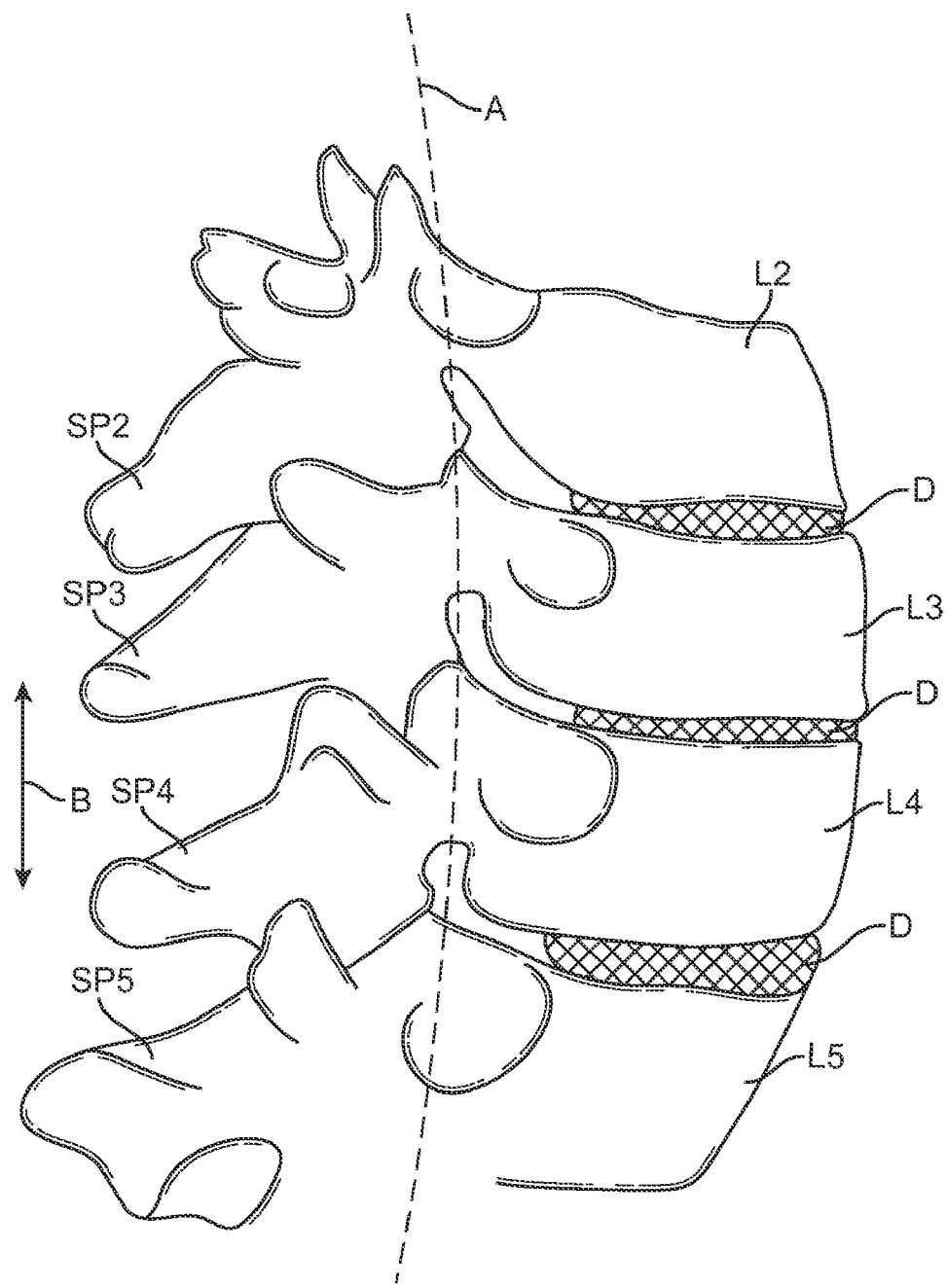
FIG. 1B a schematic illustration showing a portion of the lumbar region of the spine taken along a capital plane.

FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that may be referred to in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Figure 2:
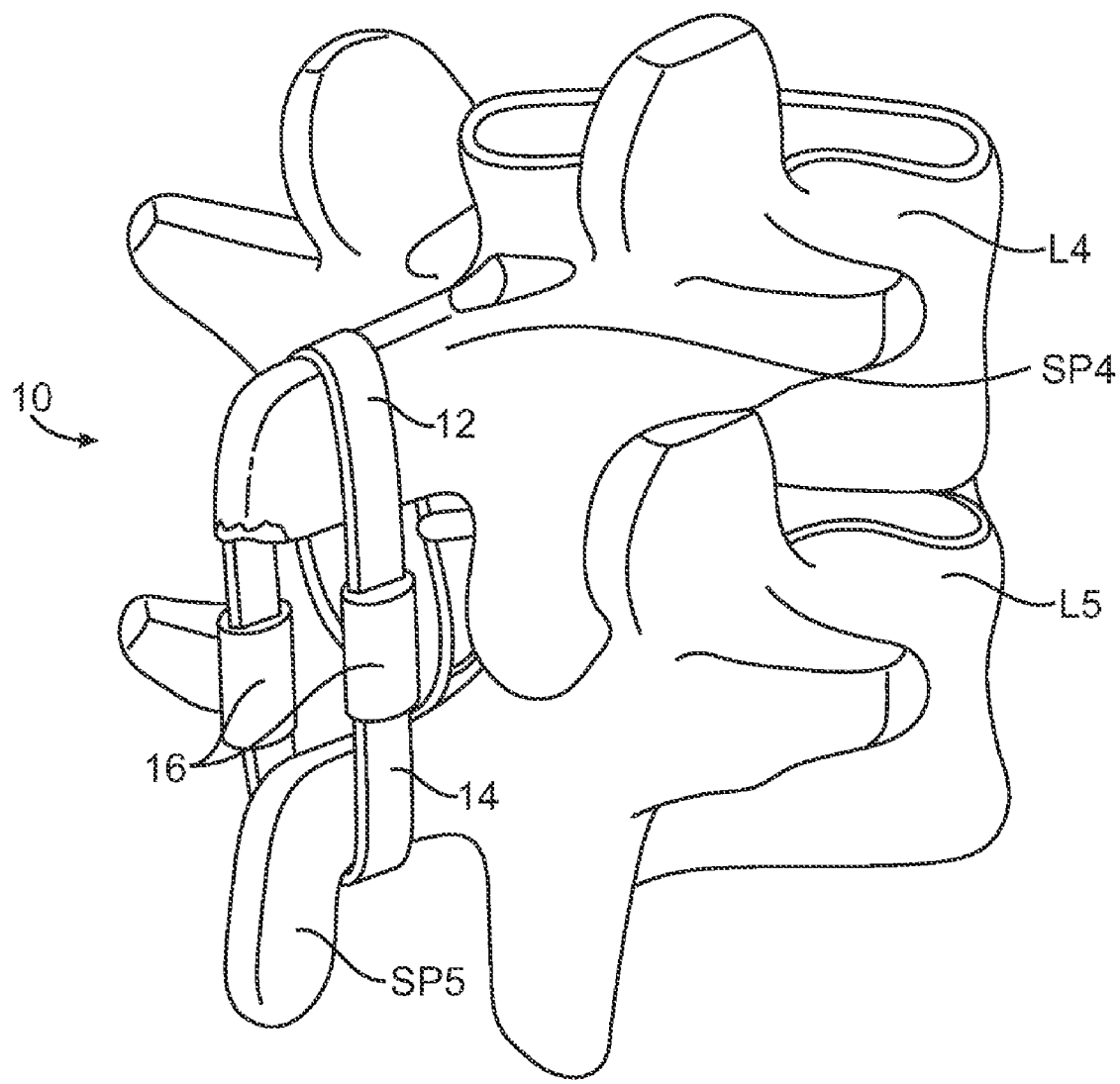
FIG. 2 illustrates a spinal implant of the type described in US 2005/0216017A1.

FIG. 2 shows a spinal implant of the type described in related U.S. Patent Publication No. 2005/02161017 A1 (now U.S. Pat. No. 7,458,981), the contents of which are herein incorporated by reference. As illustrated in FIG. 2, an implant 10 typically comprises an upper strap component 12 and a lower strap component 14 joined by a pair of compliance members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance members 16.

Figure 3A:
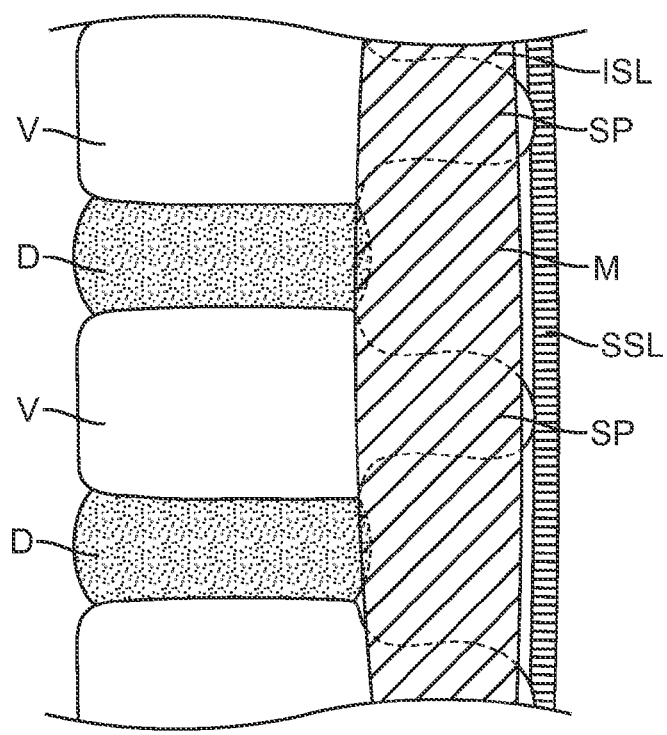
FIGS. 3A-3B illustrate additional tissue surrounding the spinous processes.
Figure 3B:
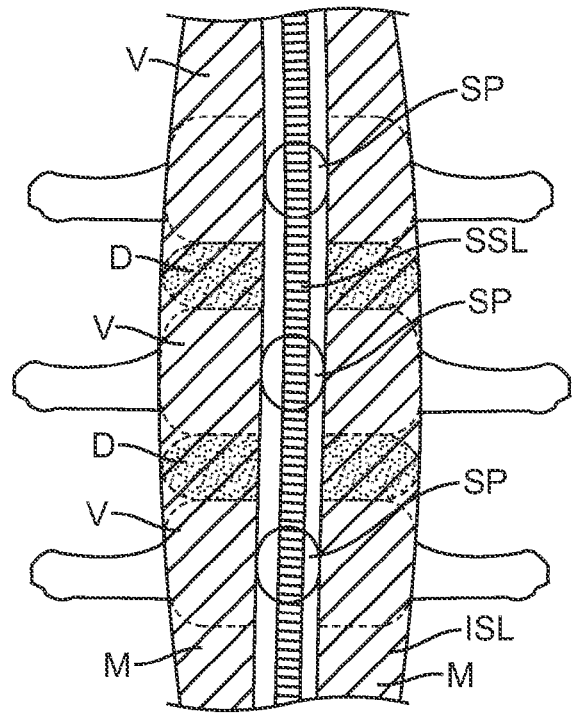

FIG. 3A is a side view of the lumbar region of the spine having discs D separating the vertebral bodies V. The supraspinous ligament SSL runs along the posterior portion of the spinous processes SP and the interspinous ligament ISL and multifidus tendon and muscle M run alongside of and attach to the spinous processes SP. FIG. 3B is a posterior view of FIG. 3A.

In order to position a constraint device around a pair of spinous processes, an upper aperture must be pierced through the interspinous ligament above a superior spinous process and at least a portion of the constraint device is then passed through the upper aperture. Similarly, a lower aperture must be pierced thorough the interspinous ligament adjacent an inferior spinous process and at least a portion of the constraint device is then passed through the lower aperture. The ends of the constraint device may then be coupled together and the device tensioned prior to closing the wound. A sharp instrument may be used to pierce the interspinous ligament and forceps or a hemostat may be used to help pull the constraint device through the apertures and across in the ligament. However, because of blood and other tissue in the operative field, it can be difficult to see or feel where to pierce the interspinous ligament relative to the spinous processes. Furthermore, it can also be difficult to capture the constraint device with forceps and therefore it may be hard for a surgeon to pull the constraint device through the interspinous ligament aperture. Improved tools may solve some of these challenges associated with implanting a spinous constraint device.

Figure 4:
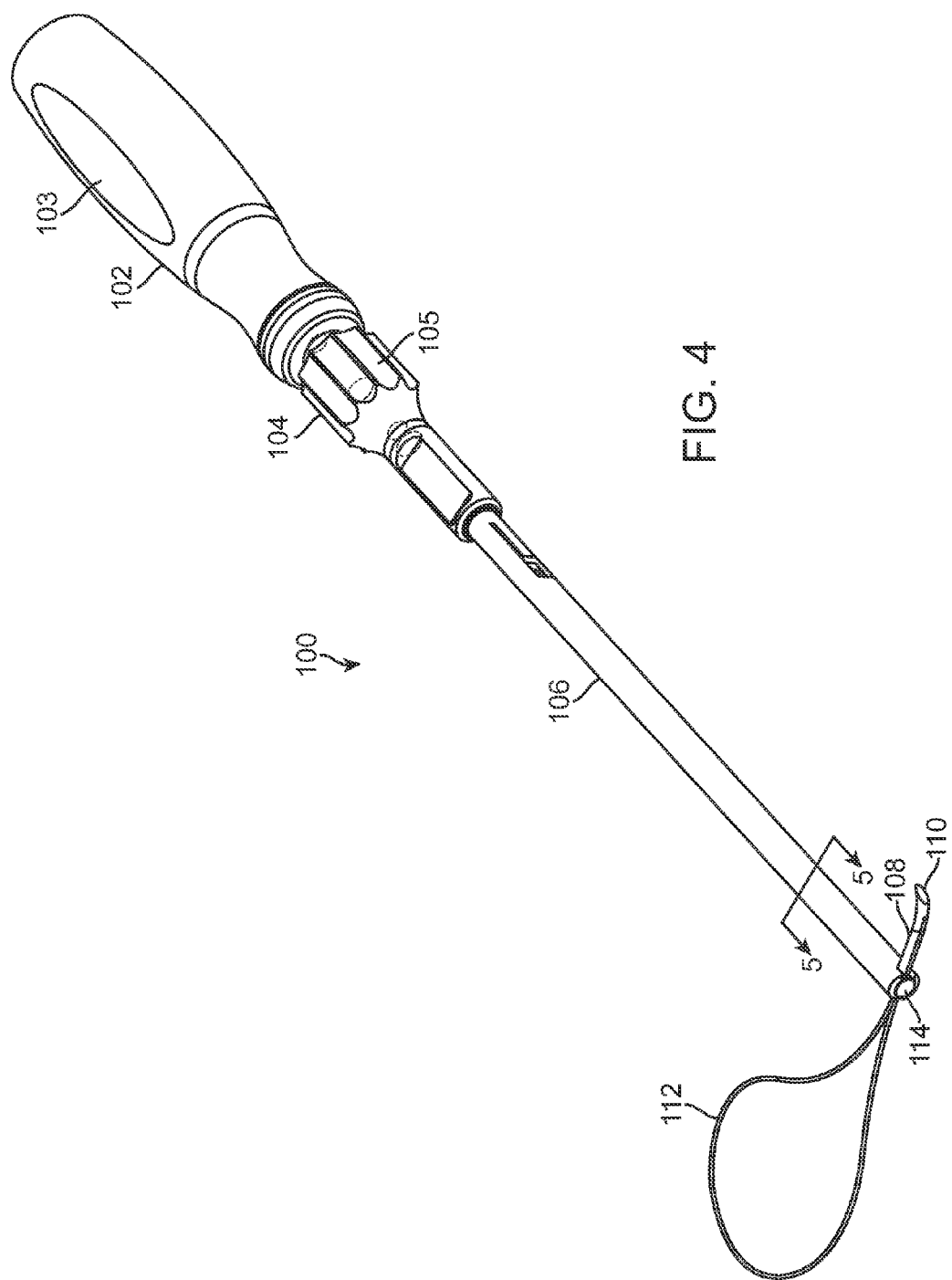
FIG. 4 shows an exemplary embodiment of a piercing tool.

FIG. 4 shows a piercing tool 100 used to help deploy a spinal constraint device around a spinous process. In FIG. 4, an elongate outer shaft 106 is coupled with handle 102 near the proximal end of the outer shaft 106. Handle 102 may have contoured regions such as flat portion 103 to provide an ergonomic fit with a surgeon's hand. Outer shaft 106 has an inner channel extending from its proximal end to its distal end and an elongate inner shaft 114 is slidably received in the channel. Actuator 104, here a rotatable knob is operatively coupled with the inner and outer shafts 106, 114 such that rotation of knob 104 linearly advances and retracts inner shaft 114 relative to outer shaft 106. Actuator 104 may have surface features such as knurling or texturing to facilitate its actuation. One of skill in the art will appreciate that motion is relative and therefore either the inner shaft 114 may move with respect to the outer shaft 106, the outer shaft 106 may move with respect to the inner shaft 114, or both shafts 106, 114 may move relative to one another. Apertures in both the outer shaft 106 and the inner shaft 114 near the distal end (best seen in FIG. 5) may therefore be aligned or offset from one another depending on the position of the inner shaft 114 relative to the outer shaft 106. The components of tool 100 may be manufactured from metals, polymers or combinations thereof. Common metals that may be used include stainless steels, titanium and the like and common polymers may include ABS, polyethylene, nylon, Teflon, PVC, Radel, Phenolic and the like.

When the apertures on both the inner shaft 114 and the outer shaft 106 are aligned, a leader, also referred to herein as a piercing element 108 may be inserted into both apertures. Then, by actuating actuator 104, the apertures may be offset from one another, thereby releasably capturing the piercing element 108. In this exemplary embodiment, the piercing element 108 includes a sharp needle-like tip 110 for piercing tissue and a wire-like filament having both ends connected to the piercing element 108 to form a loop. The loop may be used to capture and pull a surgical implant such as a spinous process constraint through tissues like the interspinous ligament during the implantation procedure. The loop may be fabricated from any number of materials such as suture, metal wires, polymer filaments and the like.

A surgeon may use the piercing tool of FIG. 4 to facilitate piercing the interspinous ligament and passing the spinous constraint device through the aperture by orienting the piercing element towards the spinous process of interest. The piercing element may be moved along the spinous process and tapped against the bone until the surgeon feels that the piercing element has passed the edge of the spinous process. The surgeon may repeat this several times until the border between the edge of the spinous process and the interspinous ligament is located and the piercing tool may then be used to pierce the interspinous ligament.

Figure 5:
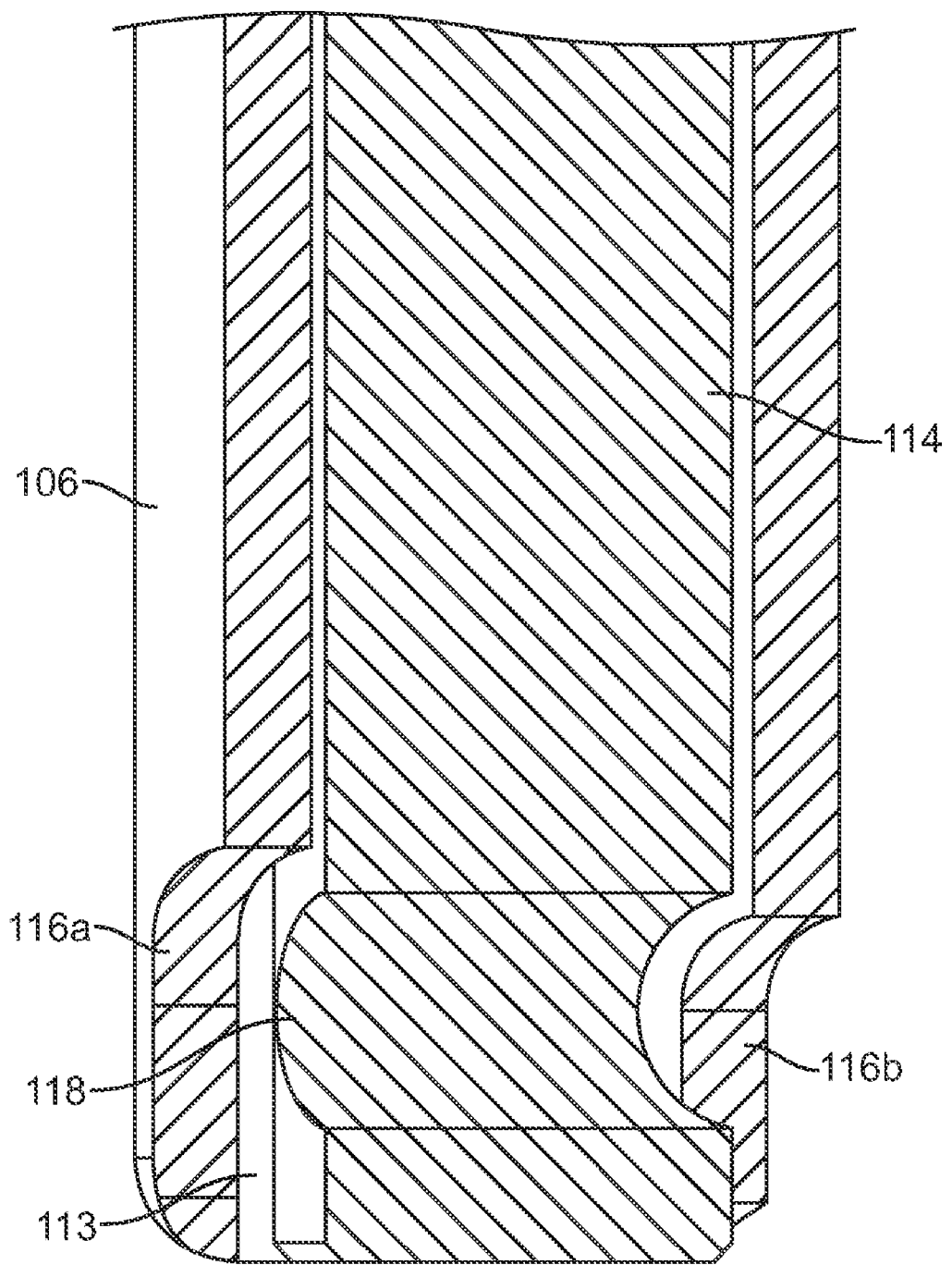
FIG. 5 shows a cross section of the tool seen in FIG. 4.

FIG. 5 shows a cross-section of tool 100 taken along the line 5-5 in FIG. 4. FIG. 5 shows inner shaft 114 slidably disposed within the channel 113 of outer shaft 106. Aperture 118 near the distal end of inner shaft 114 is sized to receive the piercing element 108. Outer shaft 106 has an entry aperture 116a on a first side of the shaft distal end and an exit aperture 116b on a second side opposite of the first side. The entry aperture 116a is larger than the exit aperture 116b thereby creating a keying feature in the outer shaft 106. The keying feature permits piercing element 108 to be received from one direction only and in some embodiments, the receiving aperture 116 in the outer shaft or the inner shaft 118 may also have additional keying features to accept the piercing element only in a specific orientation. In FIG. 5, the apertures 116a and 116b in outer shaft 106 are aligned with the aperture in the inner shaft 114 and therefore piercing element 108 may be slidably received therein.

Figure 6A:
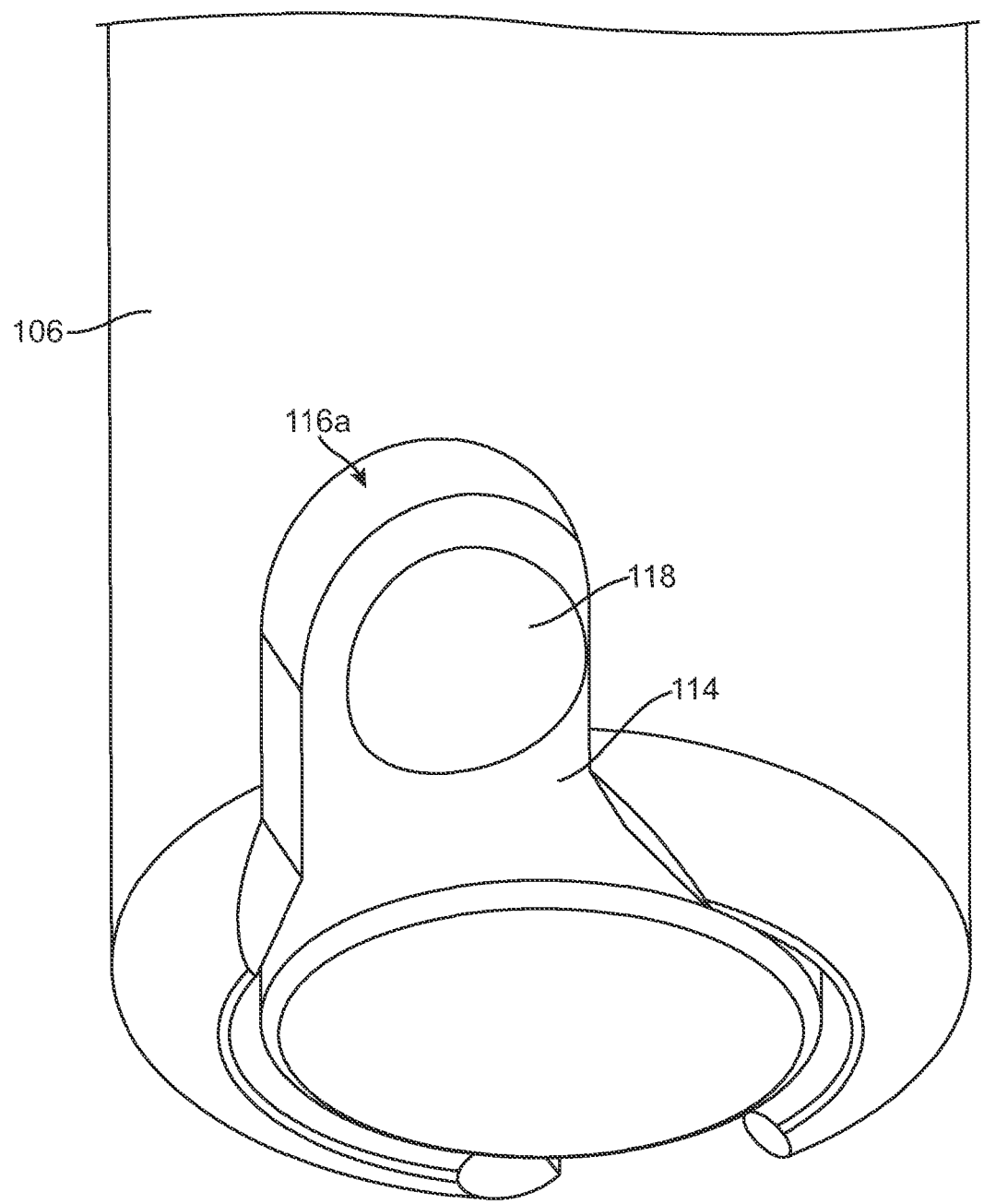
FIGS. 6A-6B illustrate the distal region of the tool seen in FIG. 4
Figure 6B:
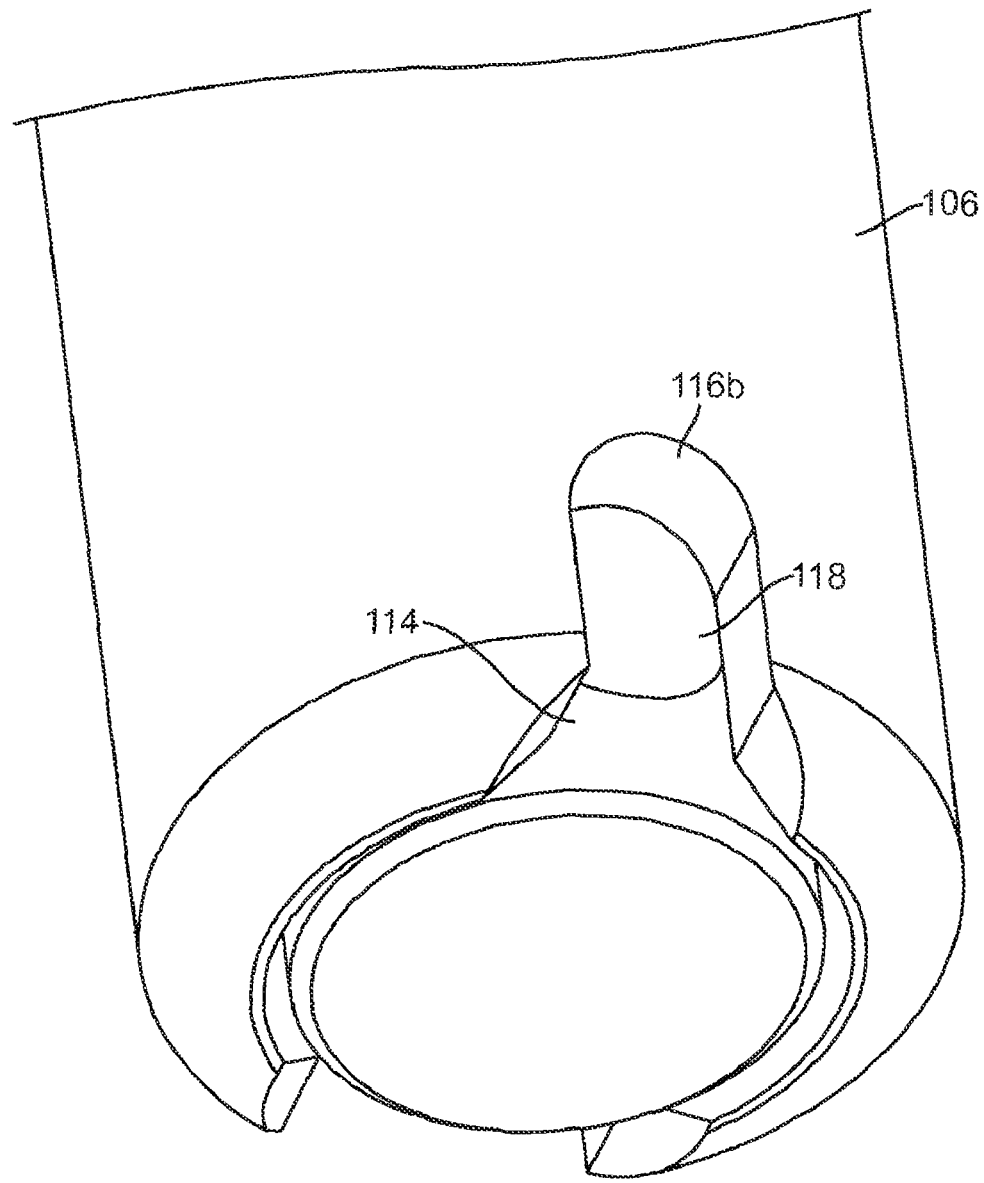

FIGS. 6A-6B illustrate perspective views of the piercing tool with inner shaft 114 slidably disposed in outer shaft 106 such that the outer shaft aperture is aligned with the inner shaft aperture for receipt of the piercing element 108. FIG. 6A is a front view showing the larger front aperture 116a in outer shaft 106 and FIG. 6B is a rear view showing the smaller rear aperture 116b in outer shaft 106.

Figure 7A:
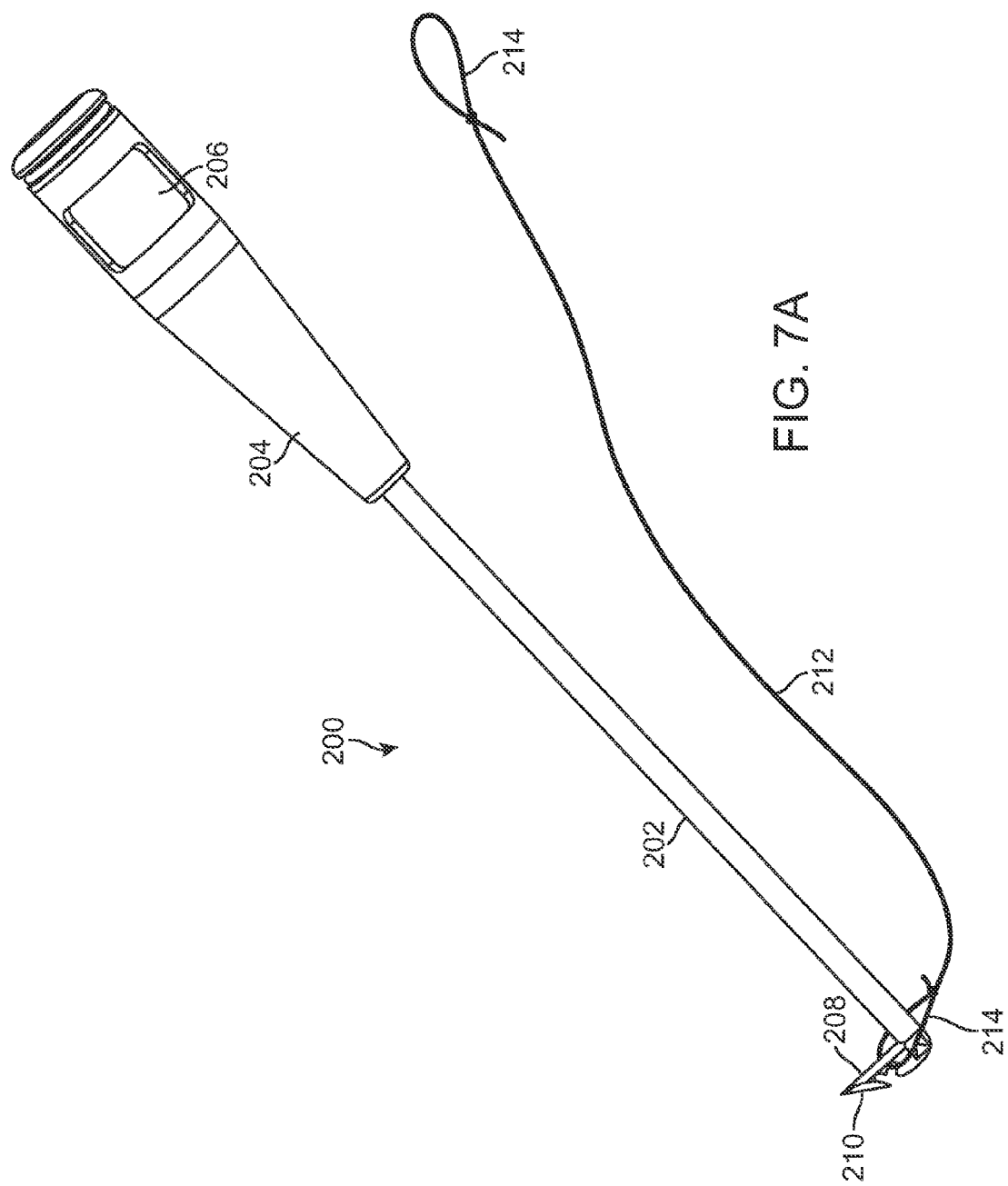
FIGS. 7A-7B illustrate another exemplary embodiment of a piercing tool.
Figure 7B:
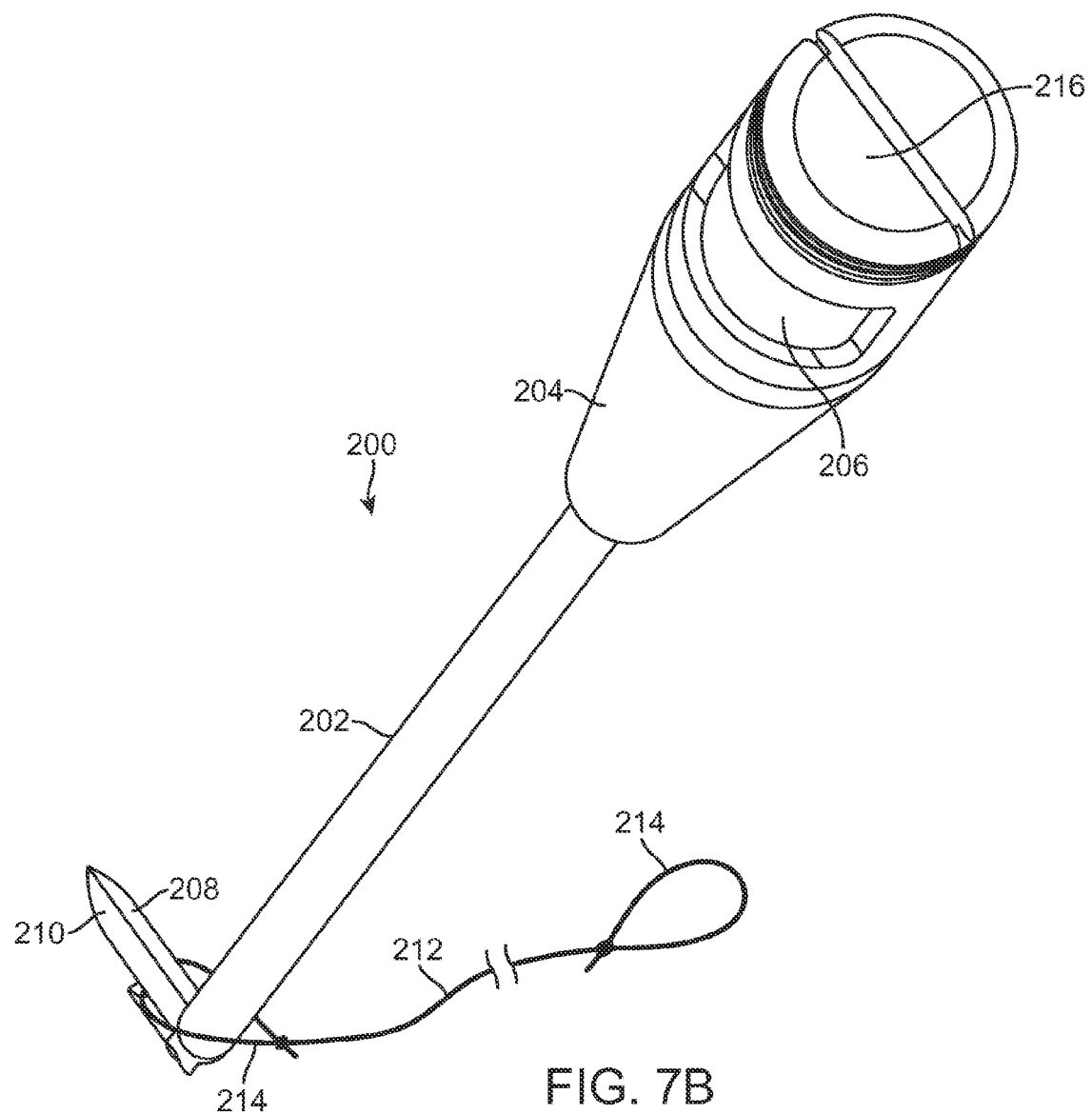

FIGS. 7A-7B illustrate another embodiment of a piercing tool that may be used to help deploy a spinal implant around spinous processes. In FIG. 7A, the piercing tool 200 comprises an outer shaft 202 coupled with a handle 204 having an actuator 206 such as a thumb wheel. A piercing element 208 having a sharp tip 210 is coupled with the outer shaft 202 and a suture 212 having loops 214 at both ends is attached to the piercing element 208. One loop 214 on the end of suture 212 is used to couple the suture with the piercing element 208 and the second loop 214 may be used to releasably grasp the spinal implant. Different knots may be used to form the loops so that the loops may be adjusted to open and close. Alternatively, a collar may be placed over the loop 214 portion of suture 212 and the collar may be slid along suture 212 to adjust loop 214. In the embodiment of FIG. 7A, piercing element 208 (also referred to as a leader) may be coupled with outer shaft 202 with a mechanism that generally takes the same form as previously described with respect to FIG. 5. Actuation of thumb wheel 206 in one direction releasably locks the piercing element 208 with the outer shaft 202 and actuation in the opposite direction releases the piercing element 208 from the outer shaft 202. In alternative embodiments, the piercing element may simply be press fit into an aperture in outer shaft 202. One of skill in the art will appreciate that a number of other coupling mechanisms may be used to releasably join the piercing element 208 with the outer shaft 202. FIG. 7B is also a perspective view of the tool 200 but at a different angle. In FIG. 7B, additional features may be included in handle 204 such as a cavity 216 which may be used to hold the unattached loop 214 of suture 212 in order to help keep it out of the surgical field.

Figure 8:
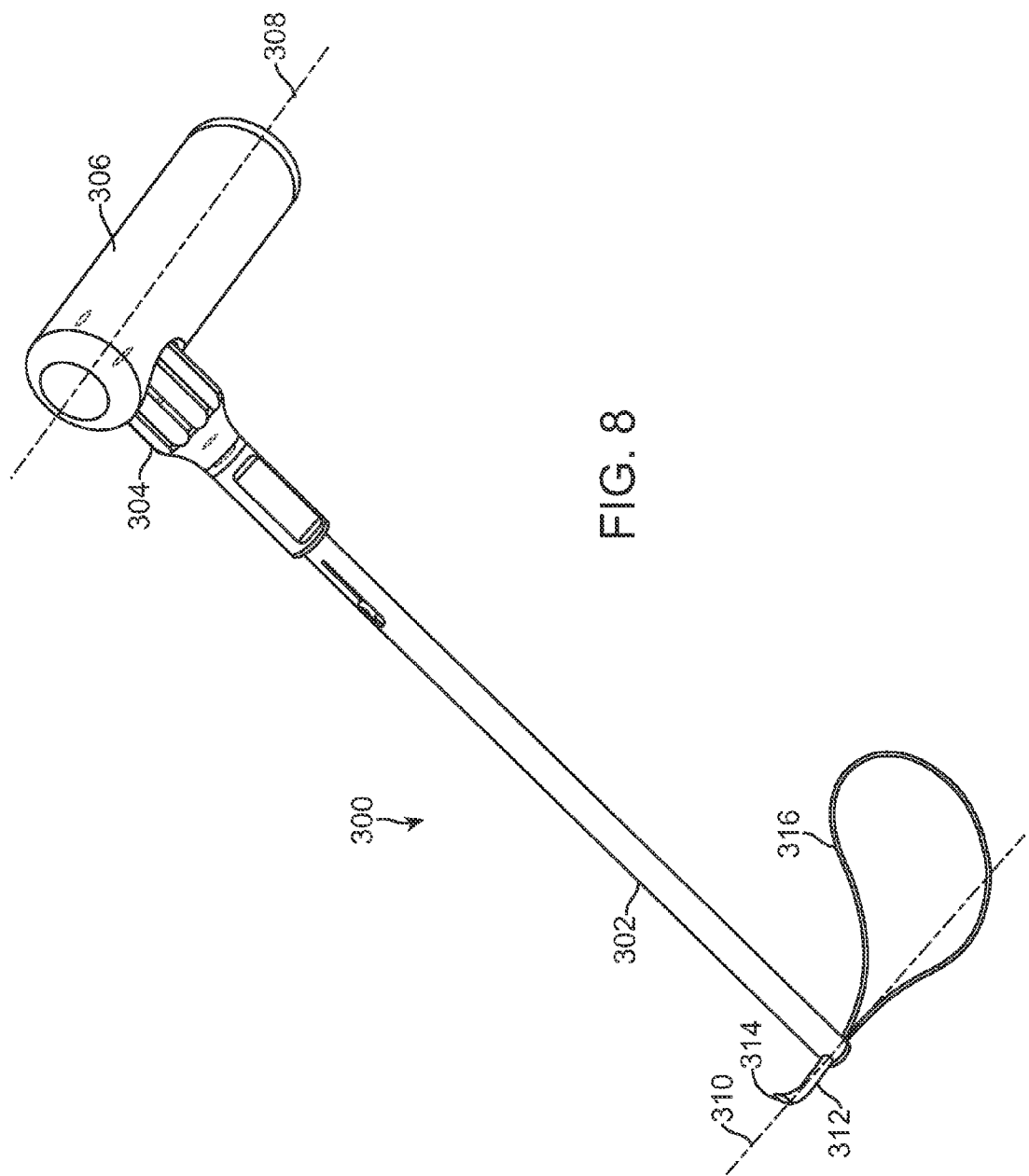
FIG. 8 illustrates yet another exemplary embodiment of a piercing tool.

FIG. 8 illustrates still another embodiment of a piercing tool. In FIG. 8, piercing tool 300 has an elongate outer shaft 302 coupled with an actuator knob 304 and pistol grip handle 306 at the proximal end of the tool 300. A piercing element 312 (also referred to as a leader) is releasably coupled with the outer shaft 302 near the tool's distal end. Piercing element 312 includes a sharp tip 314 and a loop 316 is also coupled with the piercing element 312 and may be used to grasp the spinous constraint device as it is pulled through the aperture created in the interspinous ligament. Actuator 304 is a contoured knob that may rotated in a first direction to lock the piercing element 312 into an aperture in the outer shaft 302. Actuator 304 may also be rotated in a second direction opposite the first in order to release the piercing element 312 from the tool 300. The tool 300 may also include an inner shaft (not shown) that is slidably received within an inner channel of outer shaft 302 similar to the embodiment of FIG. 4 and actuator 304 works in generally the same manner as previously described. The piercing element 312 may also be held by a press fit in an aperture on the distal end of shaft 302 or one of ordinary skill in the art will recognize that many other capturing mechanisms may be used such as a set screw, a locking clasp actuated by actuator 304, spring loaded detents, etc, any of which may be substituted in any of the embodiments disclosed herein.

One advantage of the embodiment illustrated in FIG. 8 is that pistol grip handle 306 has a longitudinal axis 308 that is generally parallel to the longitudinal axis 310 of piercing element 312. This allows the surgeon to know the orientation of the piercing element 312 even if the piercing element 312 cannot be seen due to blood, other fluids or tissue obstructing the field of view. Therefore, a surgeon will still be able to position the piercing tool based on the position of the pistol grip handle 306. A shortcoming of the pistol grip is that it is not easily adapted for ambidextrous use. An embodiment that overcomes some of these challenges by using a T-shaped handle is described below.

Figure 9:
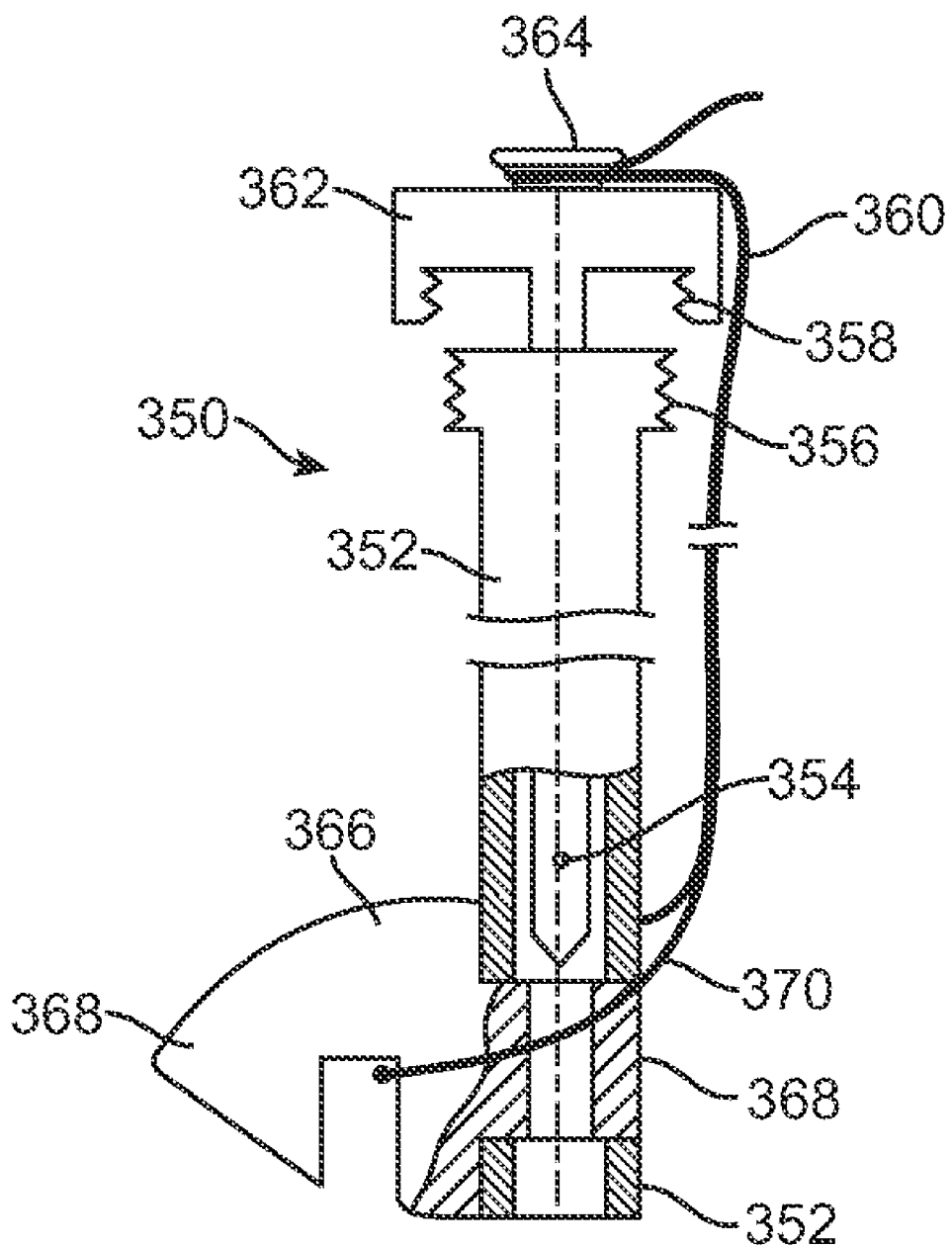
FIG. 9 illustrates another embodiment of a piercing tool.

FIG. 9 shows another exemplary embodiment of a piercing tool 350. In FIG. 9, piercing tool 350 includes an outer shaft 352 having a threaded proximal region 356. An inner shaft 354 is slidably disposed in an inner channel of outer shaft 352. Inner shaft 354 also includes an actuator knob 362 near a proximal region of inner shaft 354. Actuator knob 362 has internal threads 358 which engage outer shaft threads 356, although one will appreciate that internal and external threads may easily be exchanged with one another. A piercing element 366 (also referred to as a leader) having a sharp tip 368 is releasably coupled with the outer shaft 352. Piercing element 366 is positioned in an aperture 368 near the distal end of outer shaft 352 and then inner shaft 354 is advanced by rotation of knob 362 to lock the piercing element 366 into position. Rotating knob 362 in the opposite direction will withdraw the inner shaft 354 relative to the piercing element 366, thereby allowing the piercing element 366 to be decoupled from outer shaft 352. A suture having a loop 370 is coupled to the piercing element 366 and an opposite end of the suture 360 is wrapped around a spool 364 on the top of knob 362 in order to keep the suture's free end from dragging in the surgical field.

Figure 16A:
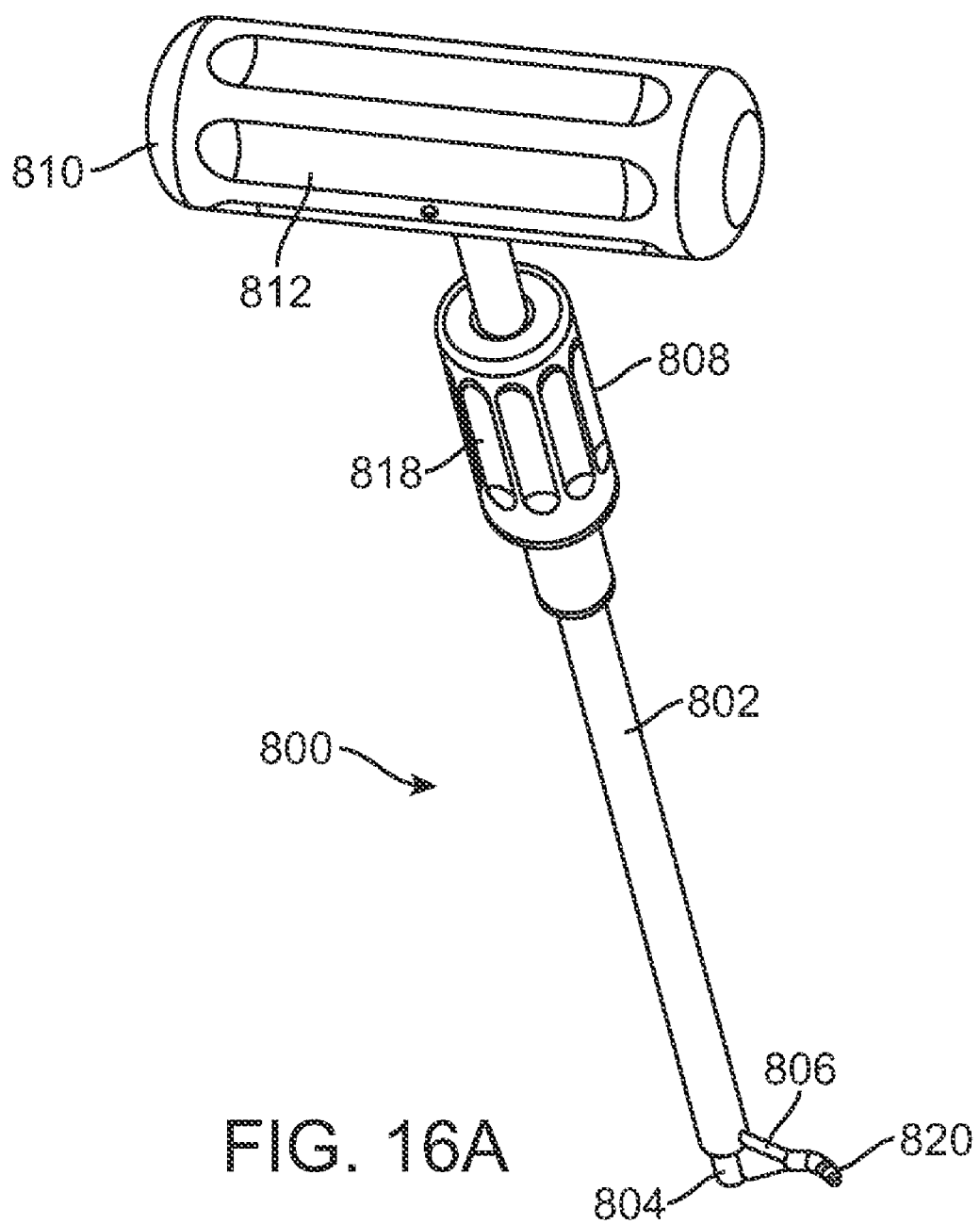
FIGS. 16A-16B illustrate another exemplary embodiment of a piercing tool.
Figure 16B:
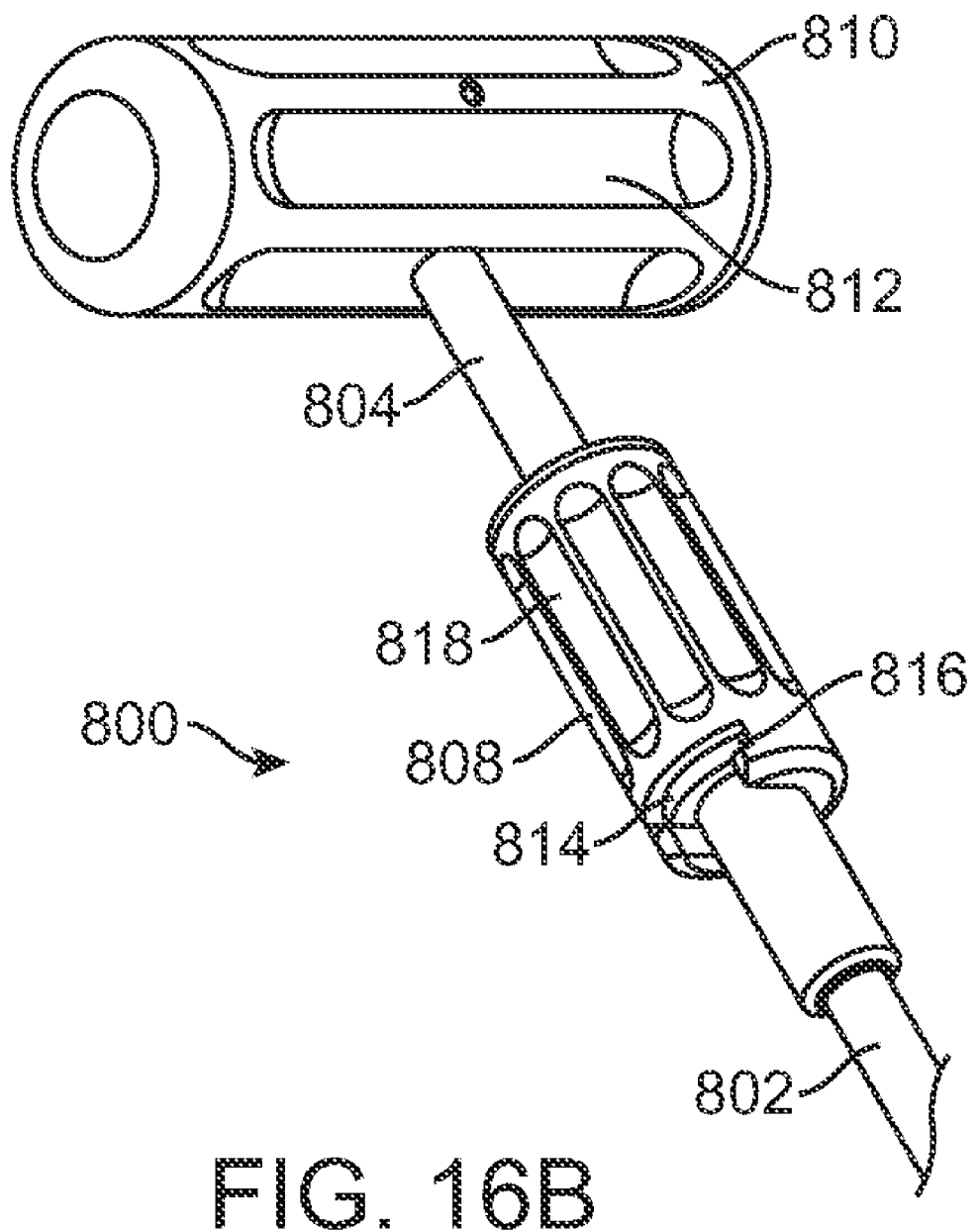

Another exemplary embodiment of a piercing tool is illustrated in FIG. 16A. In FIG. 16A, piercing tool 800 comprises an elongate outer sleeve or outer shaft 802 with a piercing element 806 (also referred to as a leader) near its distal end. The piercing element 806 has a rounded and curved tip 820 that is sharp enough to pierce the interspinous ligament without causing trauma to the surrounding bones or other tissues. Also, because of the curved shape of the piercing tip 820, piercing is preferentially performed by laterally advancing the tip into the tissue and rotating the tip in a clockwise motion to pierce the interspinous ligament. An inner shaft 804 is slidably received in the outer shaft 802 and the piercing tool is also coupled to the inner shaft 804 near its distal end. An actuating mechanism, here a thumb wheel 808 is coupled with the outer shaft 802 near its proximal end. Thumb wheel 808 may have various surface features 818 such as channels, texturing, knurling and the like in order to allow an operator to grasp or turn the wheel more easily. Thumb wheel 808 is operatively coupled with inner shaft 804 such that rotation of thumb wheel 808 will cause relative linear motion between the inner 804 and outer shafts 802. T-handle 810 is coupled with the inner shaft 804 near its proximal end and may also have surface features such as channels, texturing or knurling to facilitate grasping and manipulation 812. The longitudinal axis of the T-handle 810 is generally parallel to the longitudinal axis of the tip 820 of the piercing element 806 which helps the surgeon to know the position of the piercing element relative to the handle. The components of the piercing tool may be manufactured from any of the metals, polymers or combinations thereof that are commonly used for surgical instruments such as those described previously. FIG. 16B highlights the handle end of the piercing tool. In FIG. 16B, a flanged region 814 on the outer shaft 802 is received by a recessed region 816 in the thumb wheel 808 thereby coupling the two components together.

Figure 17A:
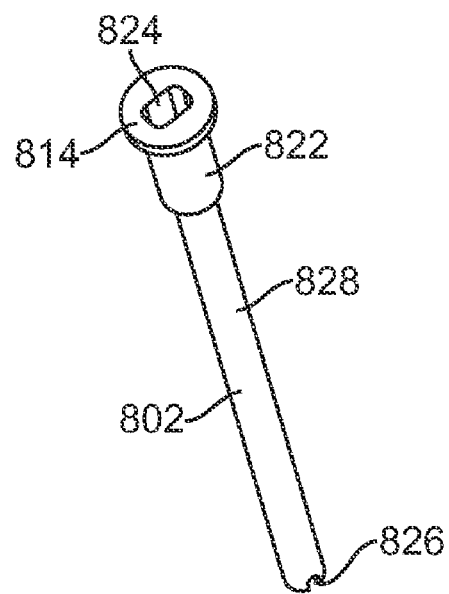
FIGS. 17A-17B illustrate an exemplary outer shaft of the embodiment in FIG. 16A.
Figure 17B:
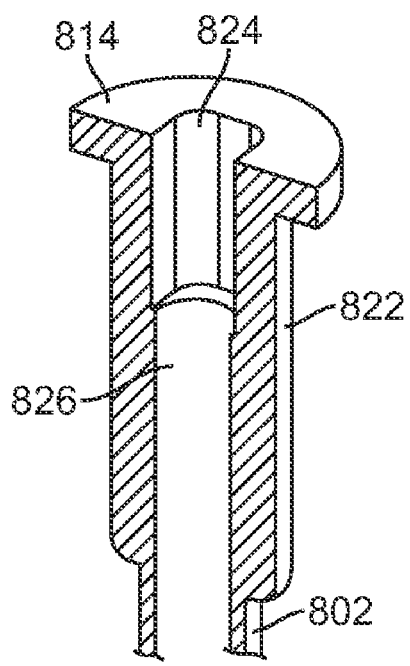

FIGS. 17A-17B illustrate the outer shaft 802 seen in FIG. 16A. An elongate main body section 828 has an aperture 826 near its distal end for receiving the piercing element 806. The proximal end of the main body 828 has a larger diameter collar 822 with the flange 824 previously described. A rectangular shaped aperture 824 is keyed so as to receive the inner shaft 804 in a specific orientation. FIG. 17B illustrates a cross section of FIG. 17A taken in the region of the flange 814 and collar 822. FIG. 17B shows the central channel 826 that extends along the outer shaft 802 in order to slidably receive the inner shaft 804.

Figure 18A:
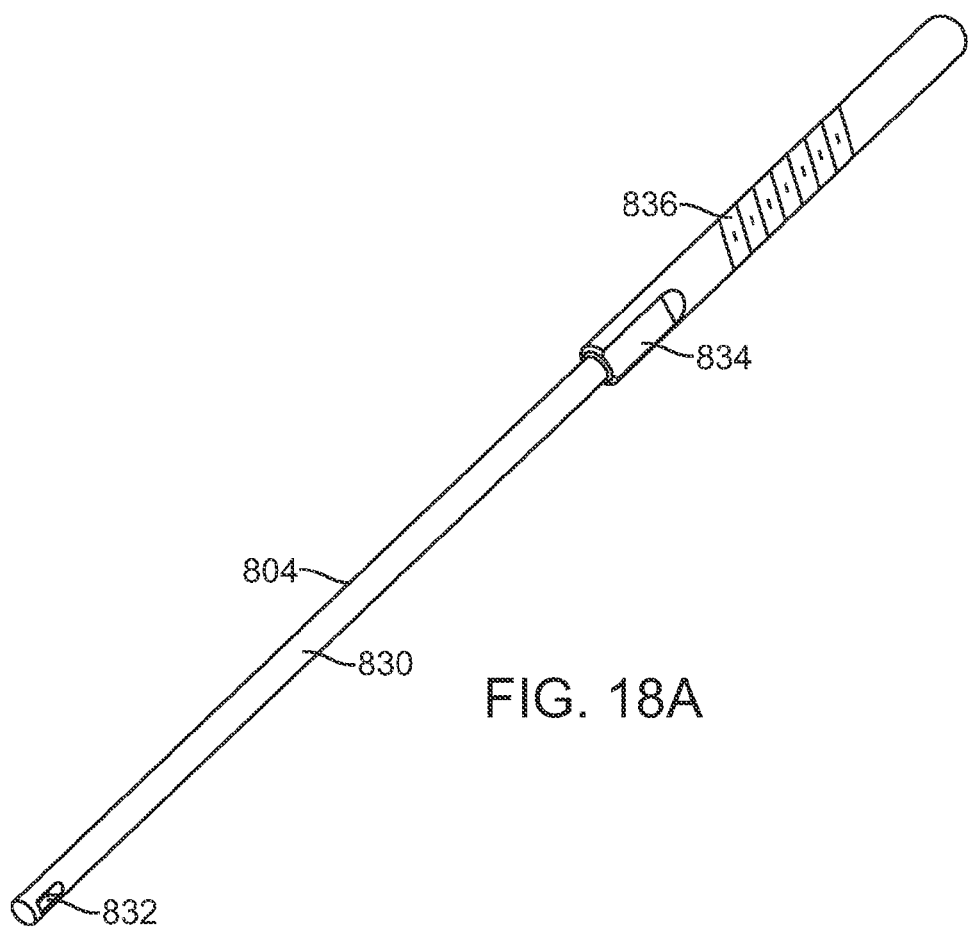
FIGS. 18A-18B illustrate an exemplary inner shaft of the embodiment in FIG. 16A.
Figure 18B:
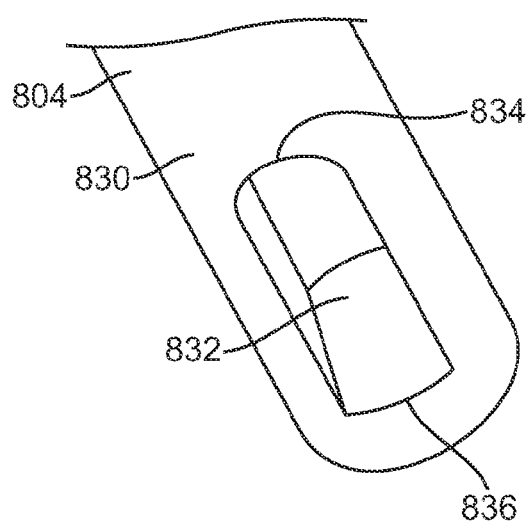

FIGS. 18A-18B illustrate the inner shaft 804 seen in FIG. 16A. Inner shaft 804 has an elongate main body 830 with an aperture 832 near its distal end. Aperture 832 is keyed to accept the piercing element 806 in a specific orientation. Here, aperture 832 has a generally rectangular shape except that one side of the aperture is arcuate 834 with the opposite side being generally flat 836. One will appreciate that many other geometries may be used to create the keying feature. FIG. 18B highlights the aperture 832 of inner shaft 804. The proximal end of the main body 830 is coupled with a flat shoulder region 834. This flat shoulder region 834 is complementary to the aperture 824 in the outer shaft 802, thus inner shaft 804 is slidably received by outer shaft 804 in a specific orientation. A proximal region of inner shaft 804 includes a threaded region 836 that can be threadably engaged with the actuator 808. The location and pitch of the threads may be adjusted as required.

Figure 19A:
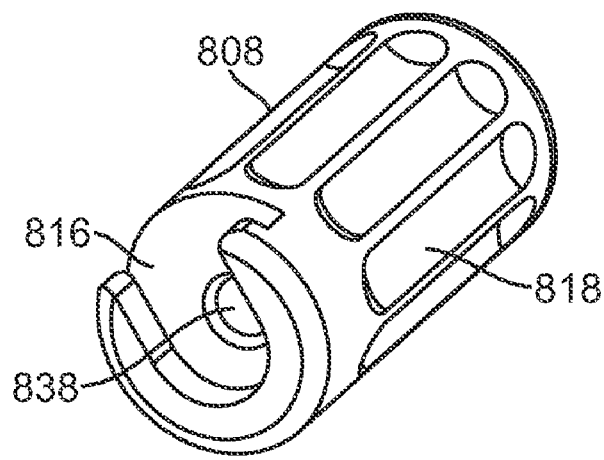
FIGS. 19A-19B illustrate an exemplary thumb wheel of the embodiment in FIG. 16A.
Figure 19B:
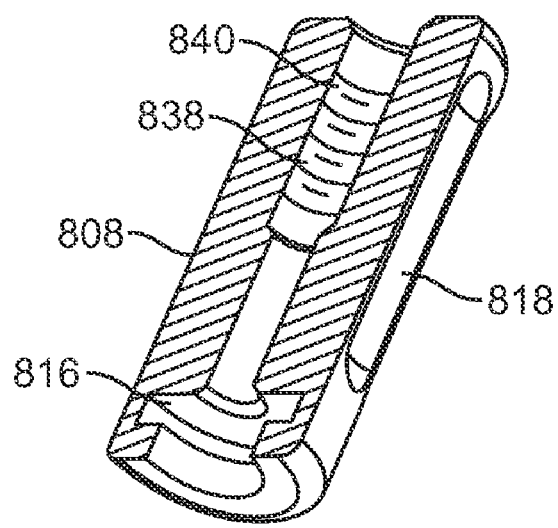

FIGS. 19A-19B illustrate the actuator 808 originally described in FIG. 16A. Actuator 808 is a thumb wheel that may be rotated to cause relative motion between inner and outer shafts 802, 804. A central channel 838 extends along the thumb wheel and is sized to receive the inner shaft 804. FIG. 19B shows a cross section of FIG. 19A and illustrates that at least a portion of central channel 838 may be threaded 840 so that thumb wheel 808 threadably engages the inner shaft 804.

Figure 20A:
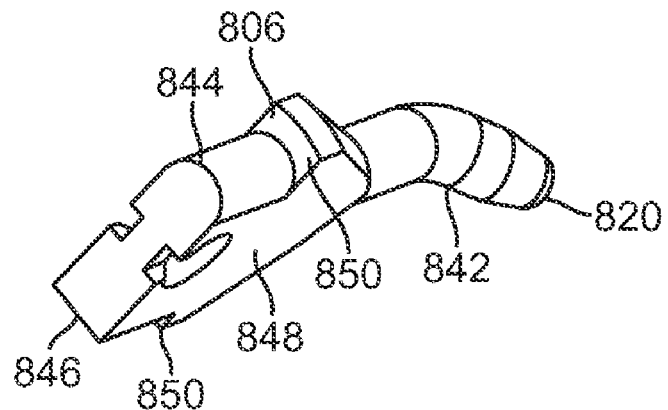
FIGS. 20A-20B illustrate an exemplary piercing element of the embodiment in FIG. 16A.
Figure 20B:
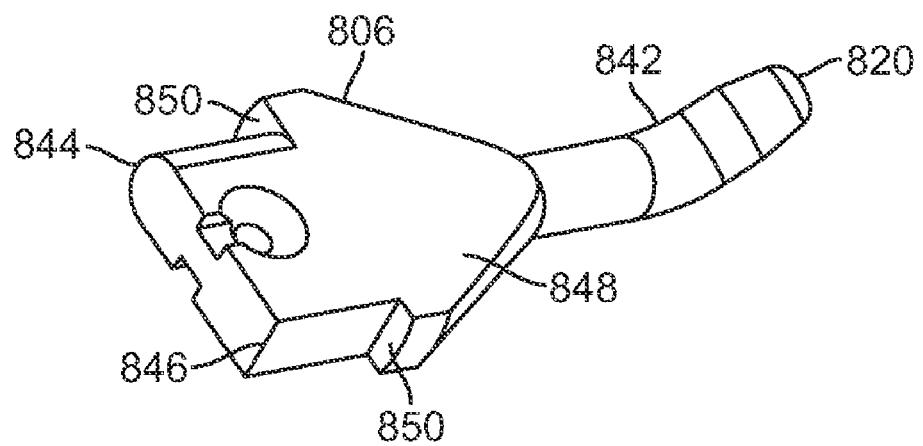

FIGS. 20A-20B illustrate an exemplary embodiment of the piercing element 806 (also referred to as a leader) seen in FIG. 16A. Piercing element 806 has a main body 848 with a coupling end that is keyed to be received by inner shaft 804. A generally rectangular shaped coupling end has a flat end 846 and an opposite curved end 844 that is complementary to and will fit into the inner shaft aperture 832 in on direction only. A wide shoulder region 850 provides a stop so that piercing element 806 can only be pressed into aperture 832 so far. The piercing end has a radius on its end 820 so that the end is not overly sharp. The tip 820 is sharp enough to allow an operator to pierce the interspinous ligament or other applicable tissue yet not so sharp as to easily result in damage to surrounding bone or other tissue. Also, it's round tip is hard enough to detect from surrounding tissue and bone by feel, but not so sharp as to puncture his surgical gloves. Furthermore, the tip is curved 842 so that the tip is biased to easily penetrate the interspinous ligament and curve around a spinous process in a clockwise direction, thereby facilitating the surgical procedure. This is advantageous since it forces the surgeon to always pass a tether or other implant in a consistent direction, here clockwise. A tapered region of the main body helps spread the tissue as the piercing element 806 is advanced through tissue. While this embodiment favors a clockwise piercing motion, the tip could also be designed to favor motion in the opposite direction or at other angles. FIGS. 20A and 20B illustrate perspective views of the piercing element 806 from two different angles.

Figure 21A:
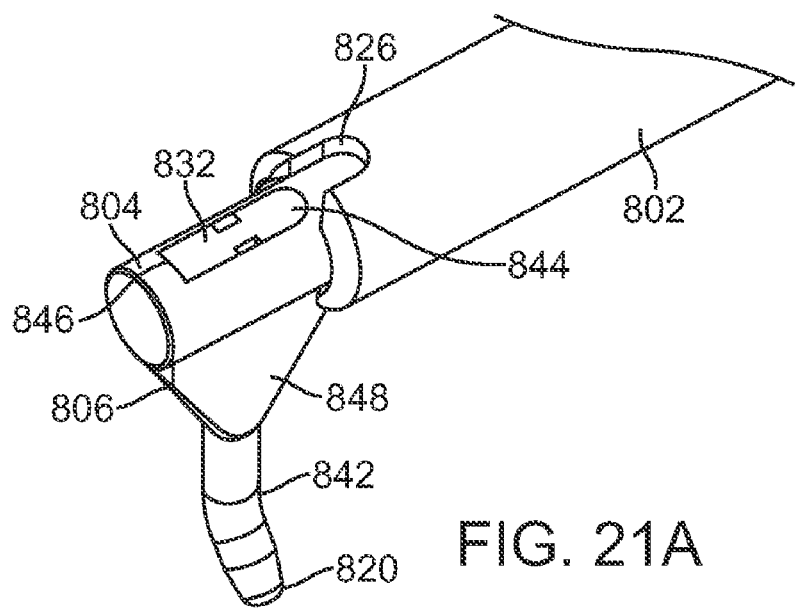
FIGS. 21A-21B illustrate coupling of the piercing element with the inner and outer shafts in the embodiment of FIG. 16A.
Figure 21B:
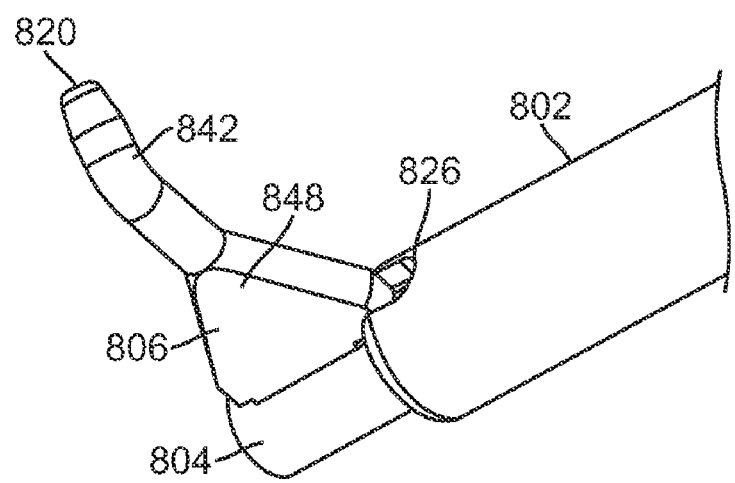

FIGS. 21A-21B illustrate how the piercing element 806 is releasably coupled with the inner and outer shafts 802, 804 of the piercing tool. In FIG. 21A, piercing element 806 is slidably received by aperture 832 in inner shaft 804. As previously discussed, piercing element 806 is keyed to fit only one way in aperture 832. In FIG. 21A, inner shaft 804 is shown extending beyond the distal end of outer shaft 802. This is accomplished by rotating thumb wheel 808 in a first direction to cause relative motion between the two shafts 802, 804. In FIG. 21B, thumb wheel 808 is rotated in a direction opposite the first so that inner shaft 804 is retracted into outer shaft 802 (or outer shaft 802 is advanced toward the distal end of inner shaft 804). The thumb wheel 808 is actuated until the piercing element 806 is captured in aperture 832 and aperture 826. Rotation of the thumb wheel in the first direction will similarly release the piercing element 806.

Figure 22:
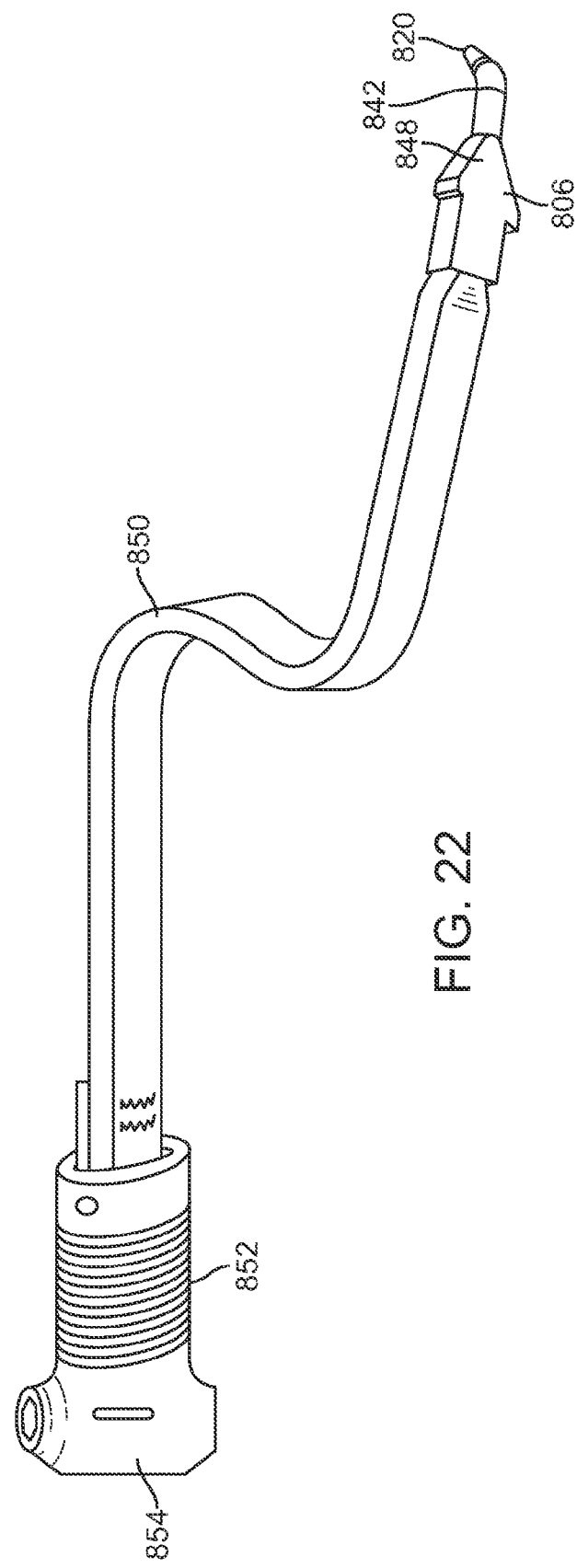
FIG. 22 shows a tether coupled with a piercing element and a locking mechanism.

A tether 850 may be releasably or fixedly coupled to the piercing element 806. For example, in FIG. 22, tether 850 is fixedly coupled with piercing element 806. The tether may be crimped, bonded or otherwise attached to the piercing element 806. The tether may be severed from the piercing element when desired. FIG. 22 also illustrates the tether 850 coupled with an optional compliance member 852 and a locking mechanism 854 that may be used to receive and lock the end of tether 850 or another adjacent tether. In other embodiments, the tether 850 may be releasably coupled with the piercing element, such as with the closeable loops described below.

As previously discussed, after the piercing element has pierced and been partially passed through the interspinous ligament, a pair of forceps or a hemostat may be used to grasp the piercing element and pull it or push it through the aperture along with the spinous process constraint device so that a free end of the device is readily accessible. However, often it is difficult to see the piercing element and therefore it may be difficult to grasp due to blood and other tissue in the operative field. Therefore, it is advantageous to have a tool that may be easily manipulated by a surgeon so that the tool may engage and capture the piercing element and pull or push it through the aperture in the interspinous ligament along with the spinous process constraint device.

Figure 10A:
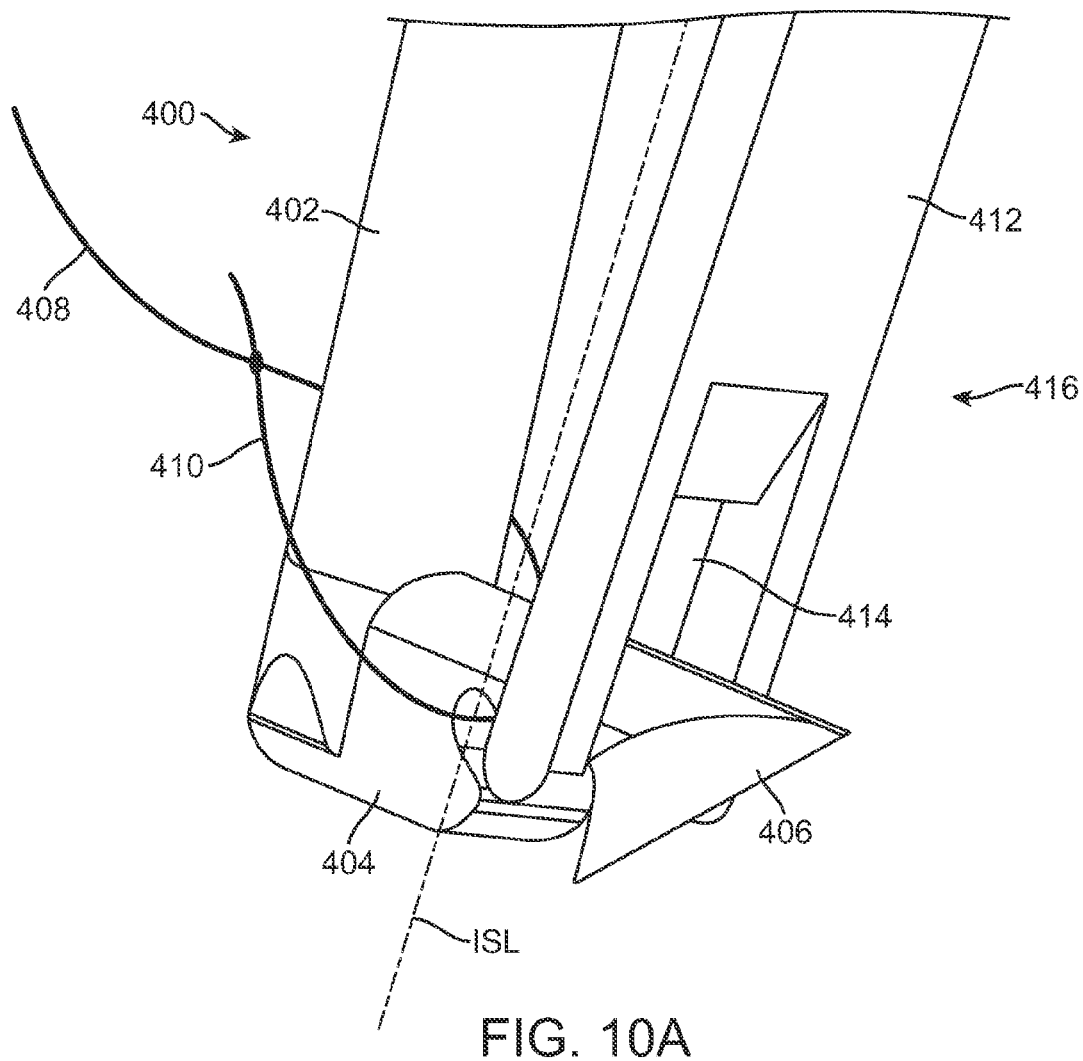
FIGS. 10A-10B illustrate release of the piercing element from the piercing tool and capture of the piercing element by a capture arm.
Figure 10B:
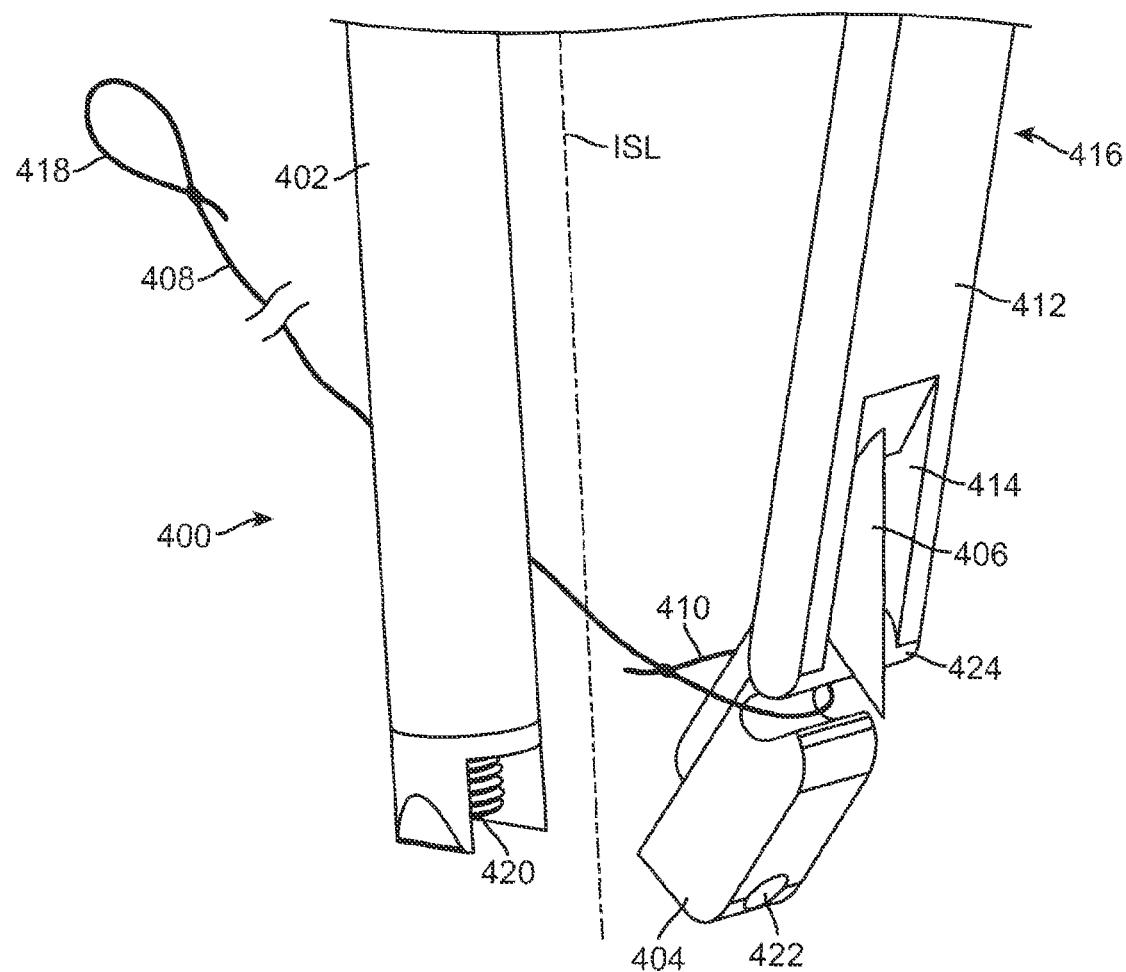

FIGS. 10A-10B illustrate one exemplary embodiment of a capture and grasping tool that may be used in conjunction with any of the piercing tool embodiments previously disclosed. In FIG. 10A, piercing tool 400 has an elongate outer shaft 402 with a piercing element 404 (also referred to as a leader) releasably attached to its distal end. A suture 408 with a loop 410 on one end is coupled with the piercing element 404. Piercing element has a sharp tip 406 that has pierced the interspinous ligament, indicated by dotted line ISL, thus a portion of the piercing element 404 is on one side of the interspinous ligament ISL while the remainder of the piercing element 404 is on the opposite side of the ligament ISL. Capture and grasping tool 416 is inserted into the patient adjacent the piercing tool but on an opposite side of the interspinous ligament relative to the outer shaft 402. The surgeon then moves the capture tool 416 until the capture tool 416 engages and releasably locks with the piercing element 404. The piercing element 404 may then be released from outer shaft 402 as seen in FIG. 10B and the piercing element 404 pulled across interspinous ligament ISL along with suture 408. In this embodiment, piercing element 404 is threadably released from outer shaft by rotating threads 420 relative to aperture 422 although any of the other coupling mechanisms disclosed above may also be used. Furthermore, as capture tool 416 is withdrawn from the interspinous ligament ISL, the sharp tip 406 is withdrawn into a guard 414 in shaft 412 of capture tool 416. This prevents the sharp tip from nicking, piercing or otherwise damaging other tissue as it is withdrawn. In this embodiment, guard 414 is a recessed region of shaft 412. As the piercing element is withdrawn, it is shaped so that it pivots around a bar 424 near the distal end of shaft 412 with the sharp tip 406 moving into the recessed region 414. As the capture tool is further withdrawn, suture 408 is advanced across the interspinous ligament ISL along with a spinous process constraint device (not shown) which may be coupled with loop 418 on a proximal end of suture 408.

Figure 11A:
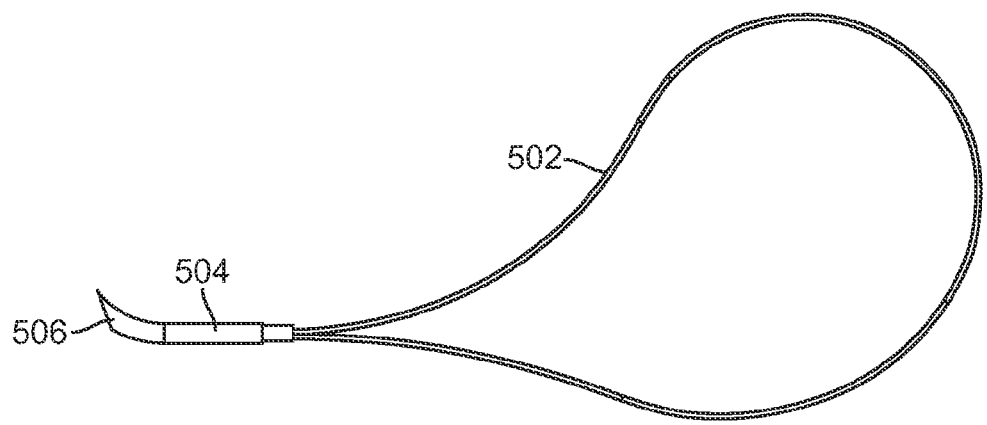
FIGS. 11A-11B illustrate an exemplary embodiment of a piercing element
Figure 11B:
Figure 12:
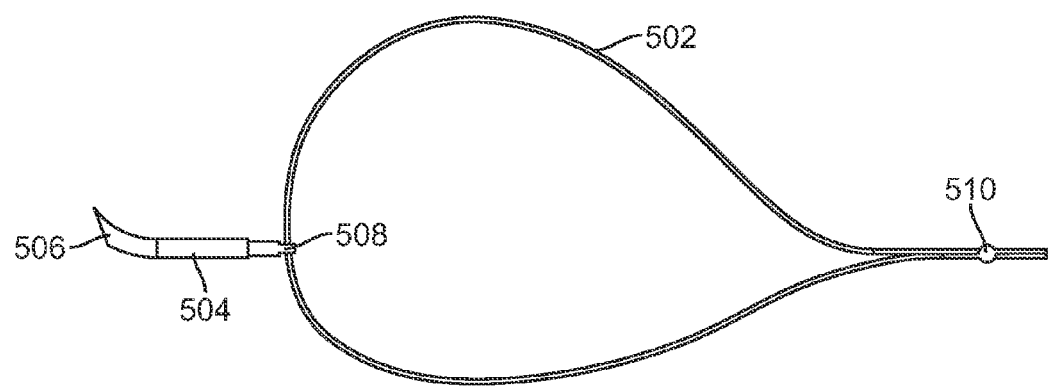
FIG. 12 illustrates another exemplary embodiment of a piercing element.
Figure 13:
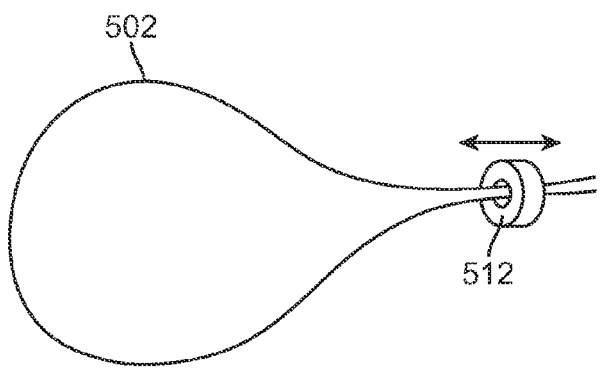
FIG. 13 illustrates the use of a collar to adjust loop size.

FIGS. 11A-11B, 12 and 13 show several exemplary embodiments of suture loops which may be used to couple the piercing element with a spinous process constraint device or any other device. In FIG. 11A, suture loop 502 is coupled with piercing element 504 (also referred to as a leader) having sharp tip 506. Both ends of suture loop 502 are crimped, adhesively bonded or otherwise attached to the piercing element 504. FIG. 11B shows a side view of the suture loop in FIG. 11A. FIG. 12 shows an alternative embodiment of a suture loop 502. In FIG. 12, suture loop 502 is threaded through an aperture 508 in the piercing element 504 and the ends of suture loop 502 are crimped together or tied together to close the loop. Thus, piercing element 504 having sharp tip 506 may slide along suture loop 502 or it may be fixed thereto. Additionally, in FIG. 13, a collar 512 may be used to help adjust loop size. In FIG. 13, collar 512 has a central aperture that is sized to fit over both ends of the suture loop 502. By advancing the collar in one direction, the loop is closed while retracting the collar in an opposite direction opens the loop up. This feature may be useful for helping to capture and release a spinous process constraint device or other device in the loop. The collar 512 may be used with any of the suture loop embodiments described herein.

Figure 14:
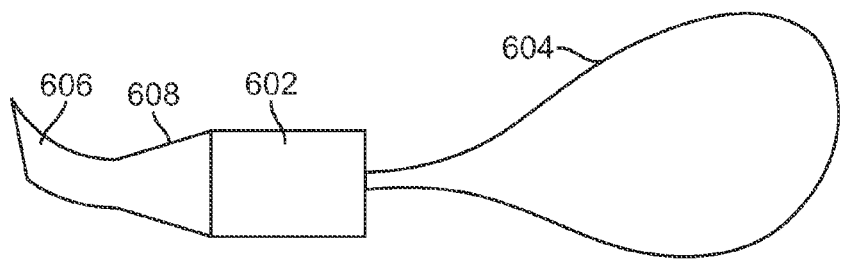
FIG. 14 illustrates still another exemplary embodiment of a piercing element.

Also, in the embodiments of FIGS. 11A-11B, 12 and 13 the sharp point section is illustrated having the same cross sectional dimension as the main body of the piercing element. Thus, as the sharp point penetrates the interspinous ligament, a small puncture is created and then it is enlarged as the tapered portion of the sharp point passes therethrough. As the rest of the piercing element passes through the interspinous ligament, the puncture size remains the same. However, in alternative embodiments such as FIG. 14, the piercing element may further enlarge the aperture. In FIG. 14, piercing element 602 (also referred to as a leader) has a sharp tip 606 that creates the initial aperture in the interspinous ligament. A tapered region 608 in the piercing element further enlarges the puncture thereby facilitating passage of the suture loop 604 through the puncture along with the spinous process constraint (not shown) attached to the suture loop 604. The tapered region may be modified to enlarge the aperture to any desired size. This feature may also be utilized in any of the piercing tool embodiments disclosed above.

Figure 27:
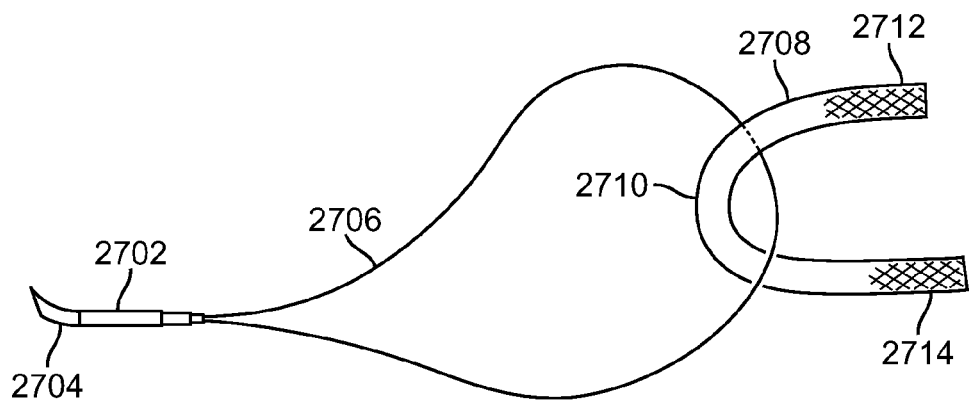
FIG. 27 illustrates looping of an implant around a portion of the leader.

One advantage of using a suture loop or lasso to capture the implant is that the free ends of the implant will be protected. This is because the implant is often looped or folded over a portion of the suture loop as seen in FIG. 27. A leader 2702 has a piercing tip 2704 and a suture loop 2706. The implant, here a tether or strap 2708 is looped around the suture loop 2706 thereby forming a new leading edge 2710 and the free ends 2712, 2714 now trail behind the new leading edge 2710 as the implant is advanced through tissue. This prevents the free ends of the strap 2708 from being frayed, bent or otherwise damaged as the implant is passed through tissue.

Figure 15A:
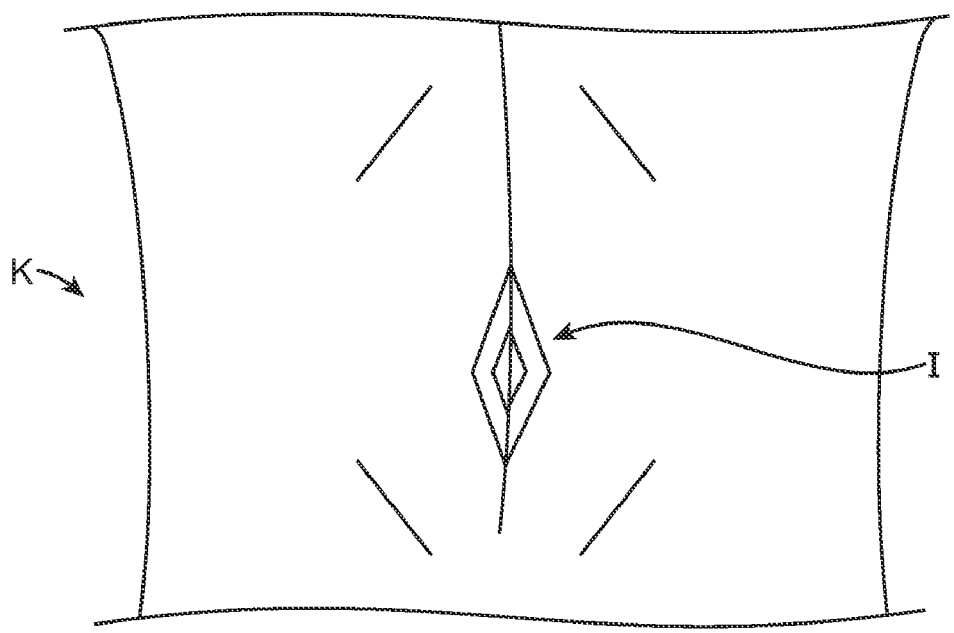
FIGS. 15A-15K illustrate an exemplary method of deploying a spinous process constraint device.
Figure 15B:
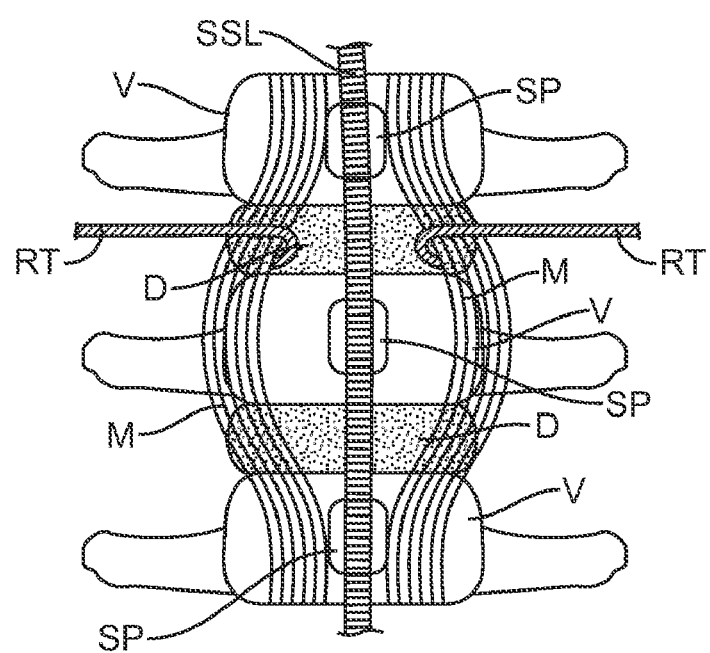

FIGS. 15A-15K illustrate an exemplary method of using the tools disclosed herein to deploy a spinous process constraint device such as the one illustrated in FIG. 2. FIGS. 15A-15K only show the most relevant anatomy in order to more clearly illustrate the deployment method. Other tissues such as muscles and tendons may not be illustrated. In FIG. 15A an initial incision is made over the spinal area of interest. FIG. 15A shows the lumbar region of back K after an incision I has been made through the patient's skin. In FIG. 15B, various tissues such as the multifidus muscle and tendon have been retracted with retraction tools RT to expose the spinous processes SP on vertebral bodies V with discs D in between adjacent vertebrae. The supraspinous ligament SSL is shown running over the tops of the spinous processes SP.

Figure 15C:
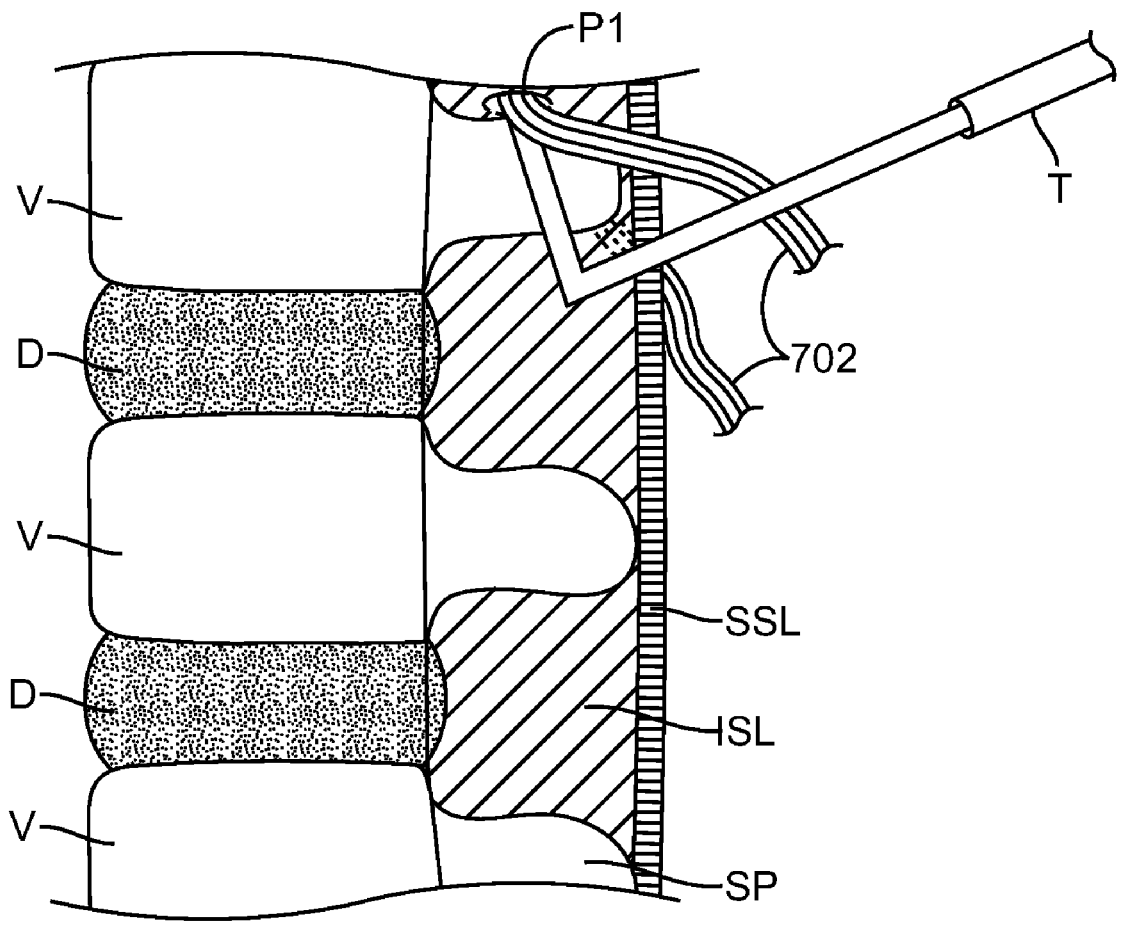
Figure 15D:
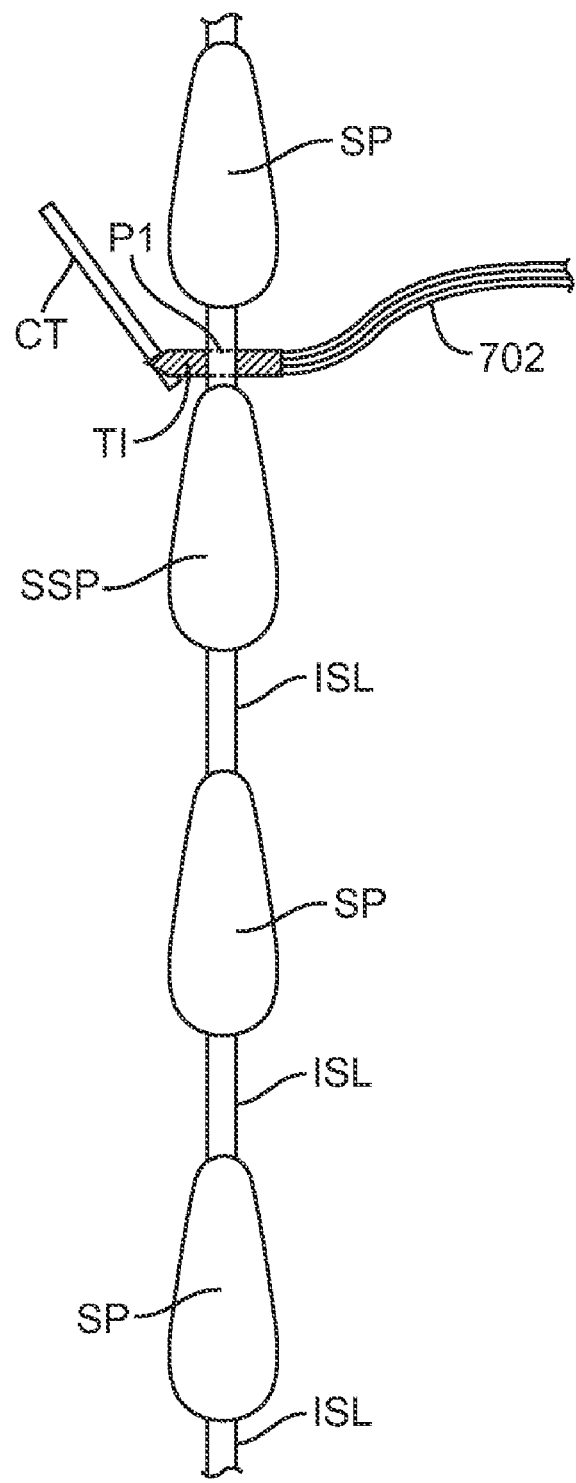

After the incision has been made, a piercing tool T having a sharp distal end may be used to access and pierce the interspinous ligament ISL while avoiding the supra spinous ligament SSL, creating an interspinous ligament perforation P1 superior of the first spinous process SSP of interest. The tip of the piercing tool may not always be a sharp needle-like tip. In some embodiments, the tip may be a rounded spherical tip with a small diameter that is still able to easily penetrate the ligament when a small force is applied to the tool, yet the tip is still blunt enough to avoid damaging other surrounding tissue and structures such as the spinous process itself. This surgical approach is desirable since it keeps the supra spinous ligament intact and minimizes damage to the multifidus muscle and tendons and other collateral ligaments. As shown in FIG. 15C, from the right side of the spine, tool T is positioned adjacent the spinous process of interest. The tip of the tool T may be tapped against the spinous process while the tool T is moved until the surgeon feels or hears a change in the tapping indicating the edge of the spinous process. This tapping process may be repeated as required until the surgeon has determined where to initiate a puncture in the interspinous ligament. The tool is then rotated slightly and advanced medially to access and pierce the interspinous ligament ISL adjacent the first spinous process SSP of interest. The distal end of tool T is shown in dotted line. Alternatively, tool T may access and pierce the interspinous ligament ISL from the left side instead. The distal end of tool T is coupled with the tether portion 702 of a spinous process constraint device, parts of which are also shown in dotted line. In addition to accessing and piercing the interspinous ligament ISL, piercing tool T also advances or threads tether 702 through perforation P1. In this embodiment, the tether portion of a spinous process constraint device is releasably coupled directly with the piercing tool. Any of the loop embodiments disclosed above, such as FIGS. 12 and 13 may also be used. These loops may be releasably attached to the piercing tool on one end and the loop portion may be cinched down to grasp the spinous process constraint device.

Figure 15E:
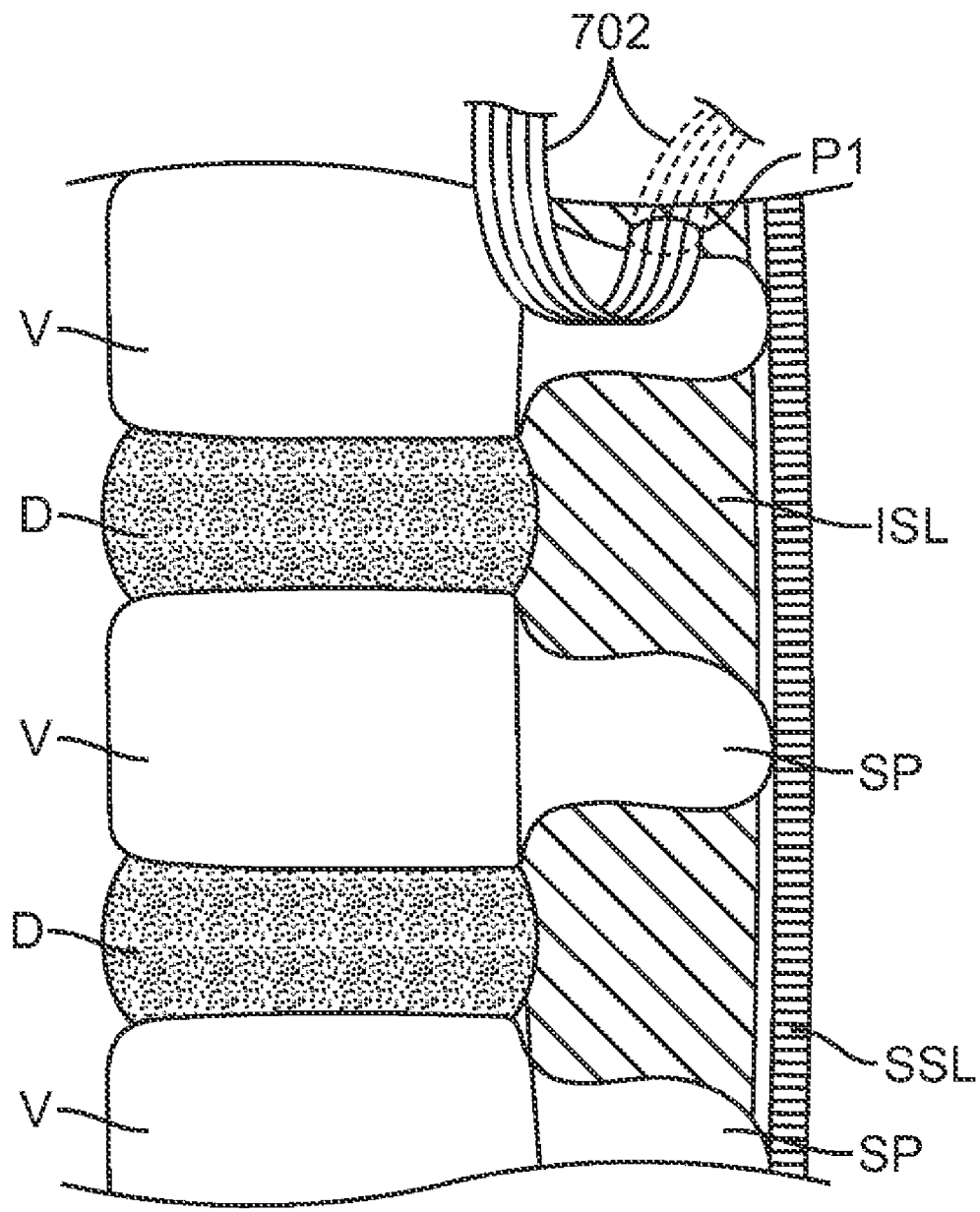

After the initial puncture is created in the interspinous ligament ISL and at least a portion of the piercing element has been advanced through the puncture, a capture tool CT such as the embodiment described above, may be used to engage and capture the piercing element TI. The piercing element TI may then be released from the rest of piercing tool T which is then removed from the patient's body, as seen in the posterior view of FIG. 15D and the capture tool pulls the piercing element and spinous process constraint device 702 across the interspinous ligament as seen in FIG. 15E. If a loop is used to couple the spinous process constraint device with the piercing element, then the piercing element is pulled across the interspinous ligament along with a sufficient length of the loop so that the physician may easily pull the spinous process constraint device across the ligament either manually or with the capture tool or other instrument. Because the spinous process constraint device is wrapped around a portion of the loop and opposite sections of the device are folded toward one another, a new leading edge is created for passage through the puncture. This is advantageous since it is less likely that the folded portion will be damaged when passing through the piercing as compared with passing either end of the constraint device through the puncture where an end can easily be frayed, bent or otherwise damaged (e.g. similar to threading a needle with the tip of a thread as opposed to threading a looped section of thread through a needle). Moreover, the piercing element or other portions of the tool and the loop may be radiopaque to facilitate observation under fluoroscopy. This helps provide valuable intraoperative information about the level and anatomy at which the implant is being deployed and also helps the surgeon confirm that the correct level is being treated and allows the edge of spinous process against which the constraint device will lie to be more clearly located.

Figure 15F:
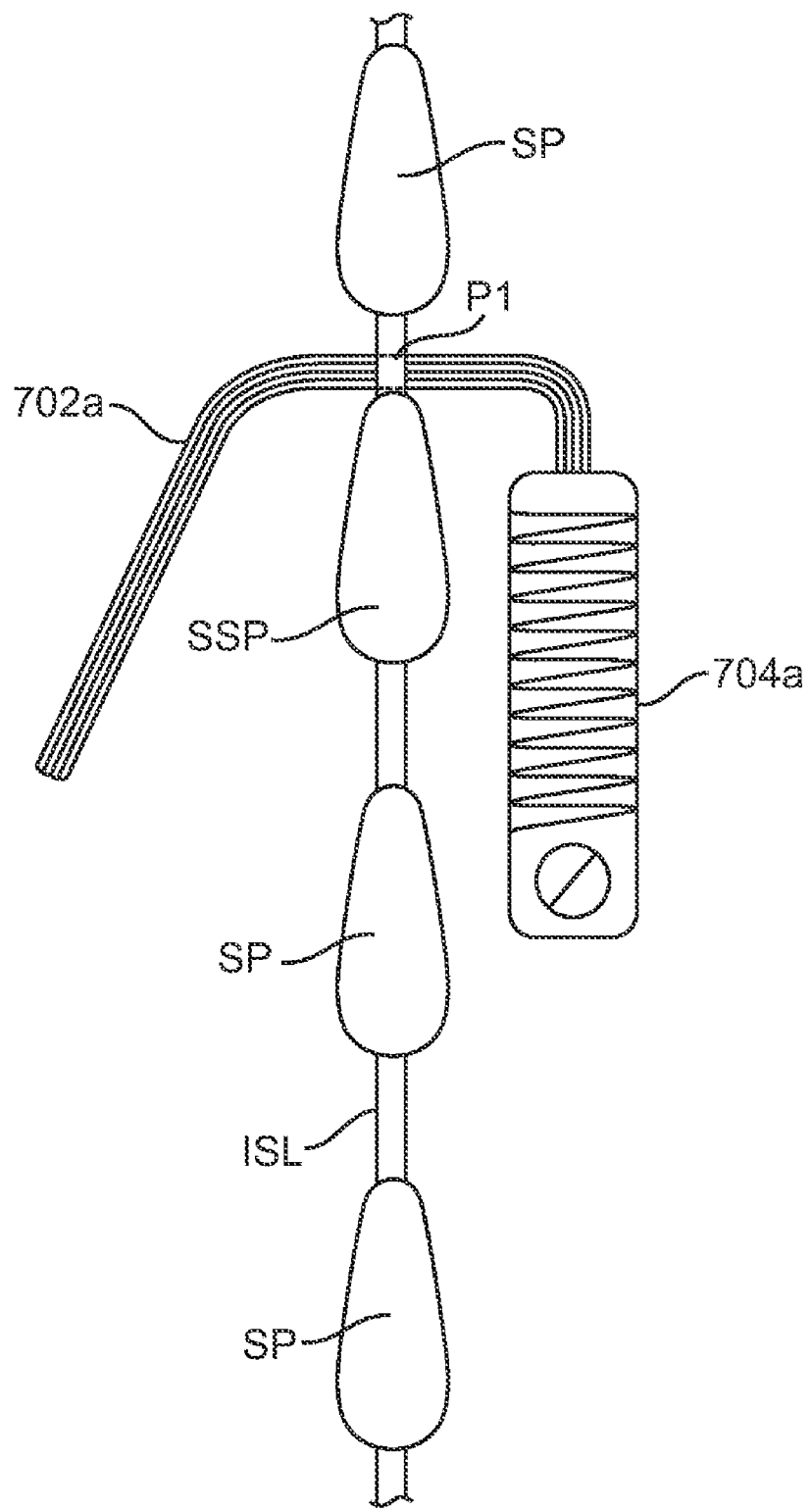

FIG. 15F illustrates a posterior view of the spinal segment with a tether portion 702a of the spinous process constraint device pulled across the interspinous ligament ISL. A compliance member 704a is left on the opposite side of the interspinous ligament ISL. Further details and other embodiments of compliance members are disclosed in commonly owned U.S. patent application Ser. No. 12/106,103, the entire contents of which are incorporated herein by reference.

Figure 15G:
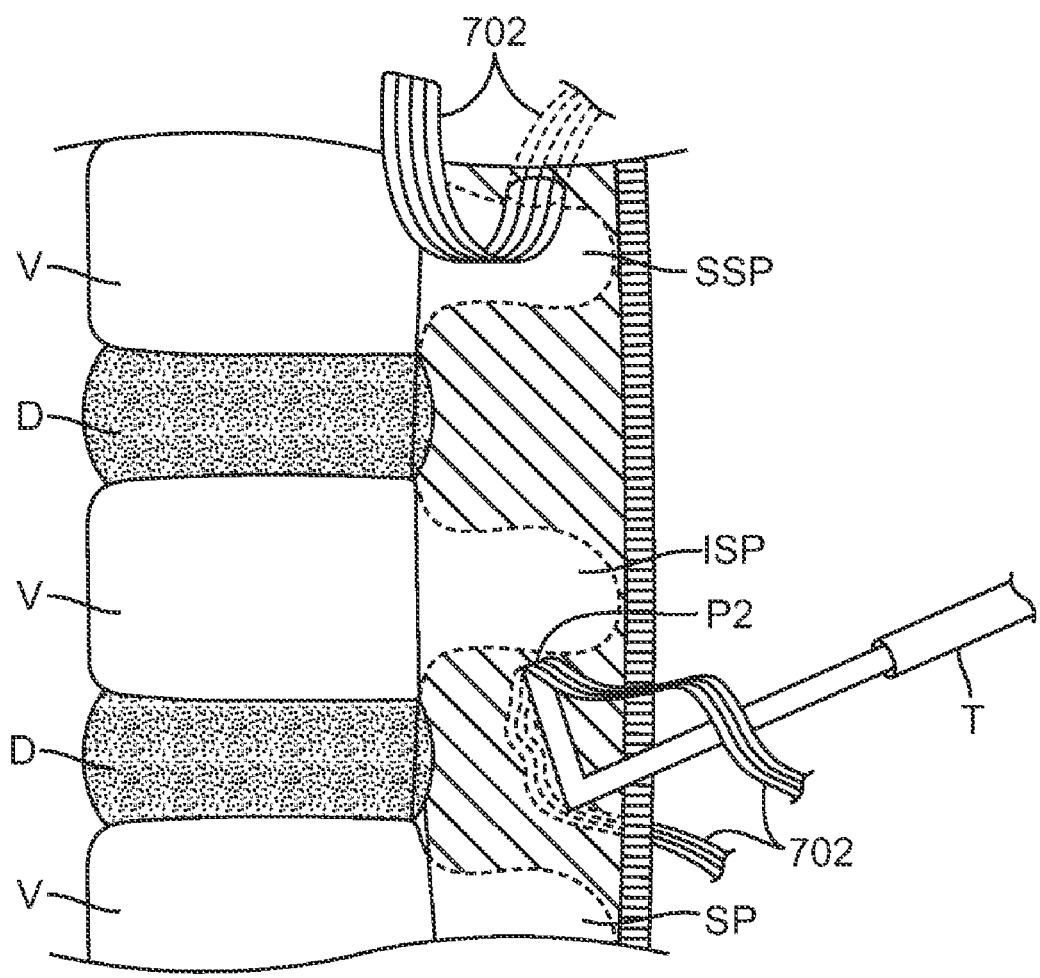

The steps of accessing the ISL, piercing the ISL, and threading tether 702 through a perforation are then repeated for the opposite, lateral side of the spine for an adjacent spinous process ISP, inferior of the first superior spinal process SSP of interest. As shown in FIG. 15G piercing tool T accesses the interspinous ligament from the left side of the spinal midline and pierces the interspinous ligament ISL, creating a second perforation P2 located inferior of a second spinous process of interest, labeled as inferior spinous process ISP. FIG. 15G illustrates the second piercing. As shown in FIG. 15G, the inferior spinous process ISP of interest is directly adjacent to and inferior of the first superior spinous process SSP of interest. However, it is entirely possible to perform the described procedure starting with the inferior spinous process ISP first instead of the superior spinous process SSP, for example, perforation P2 may be created before perforation P1. It is also possible that there may be a gap of one or more spinous processes SP between the spinous processes of interest.

Figure 15H:
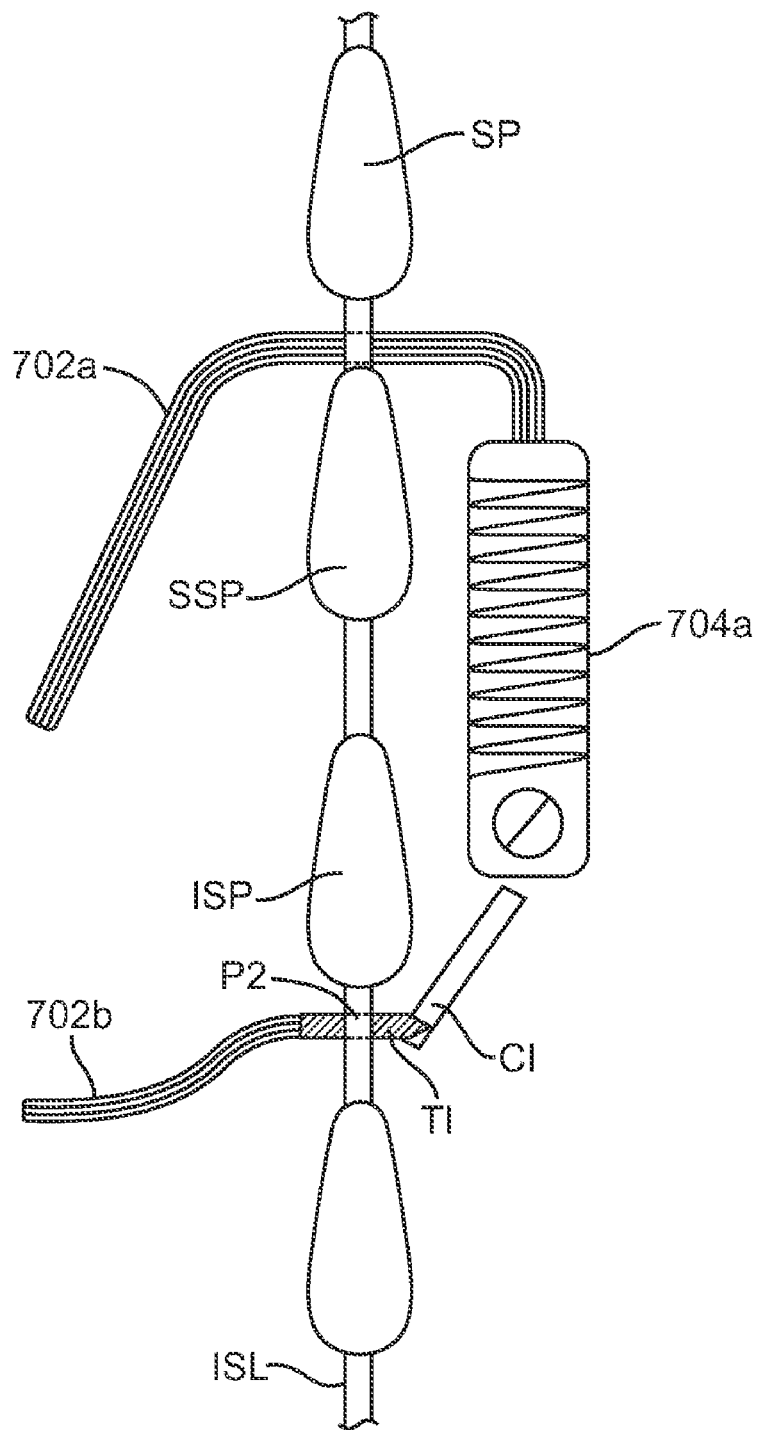
Figure 15I:
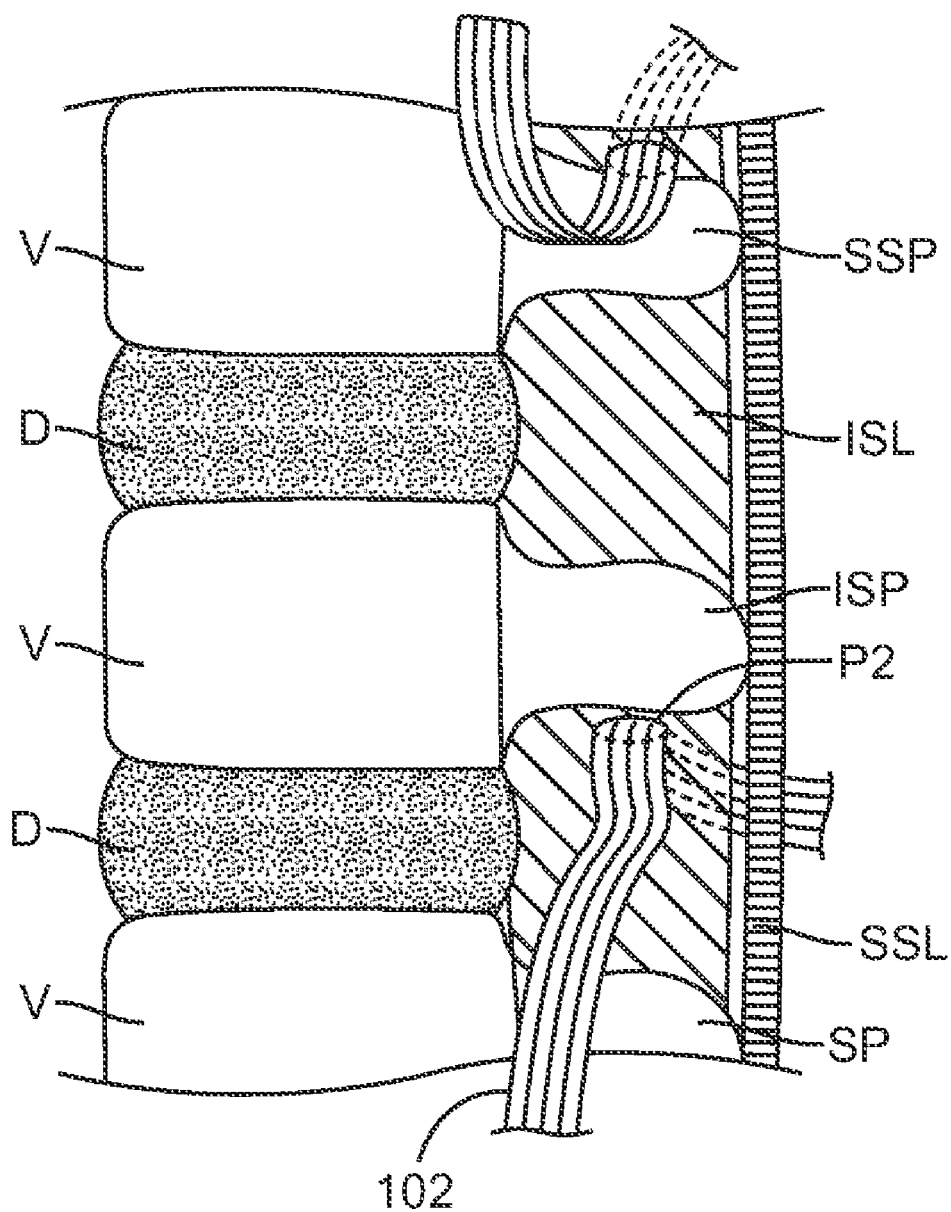
Figure 15J:
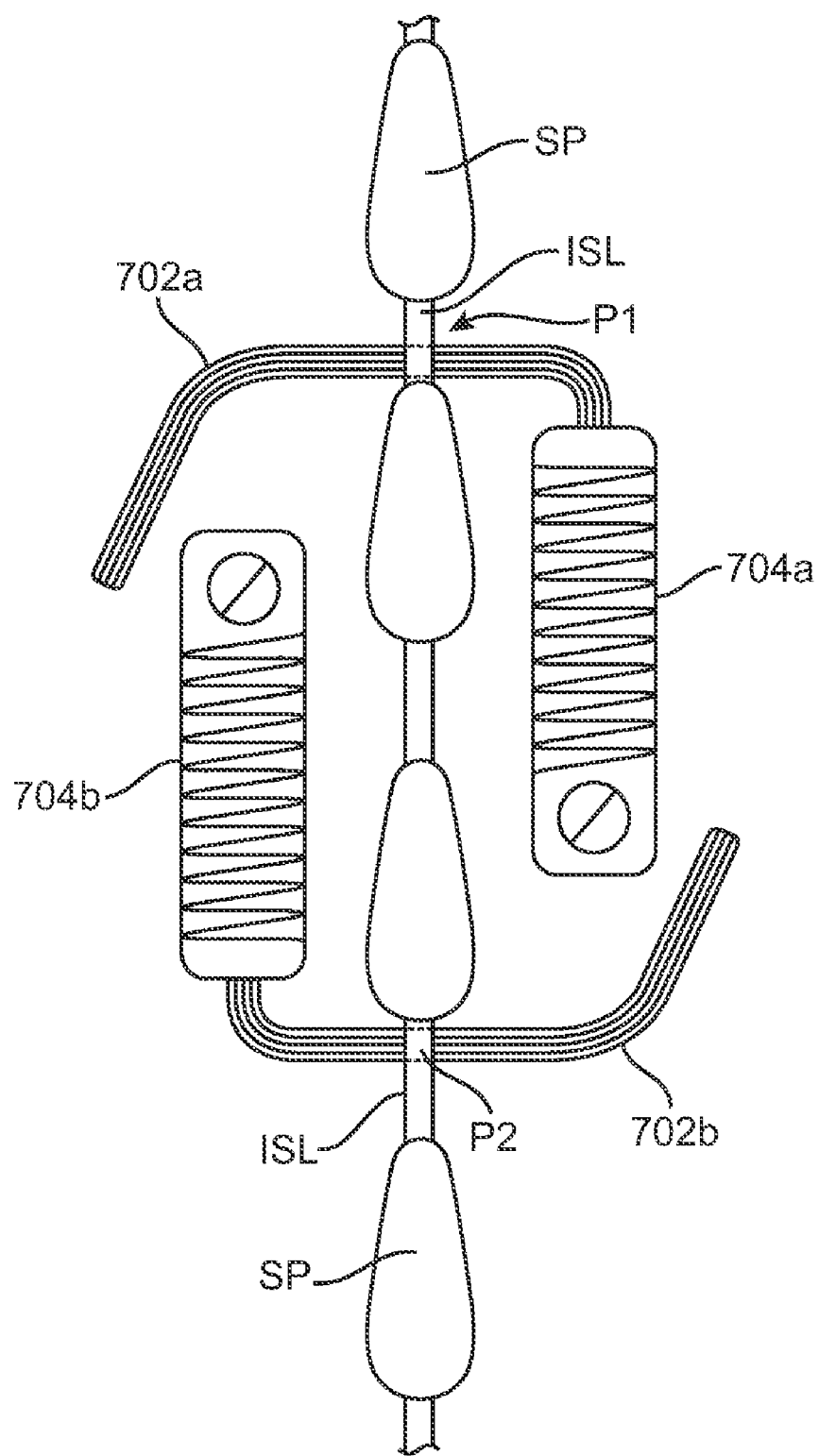

In FIG. 15H the piercing element TI is decoupled from the remainder of the piercing tool T and a capture tool CT is used to engage and grasp the piercing element TI so that the piercing element TI and second tether 702B may be advanced across the interspinous ligament as seen in FIG. 15I. FIG. 15J is a posterior view of the spinal segment showing tethers 702a and 702b crossing the interspinous ligament ISL. Again, the tether portion of the spinous process constraint device is coupled directly to the piercing element in this embodiment. A loop such as those previously disclosed may also be used to attach the tether portion with the piercing element. Each tether 702a, 702b is coupled to a compliance member 704a, 704b on opposite sides of the interspinous ligament.

Figure 15K:
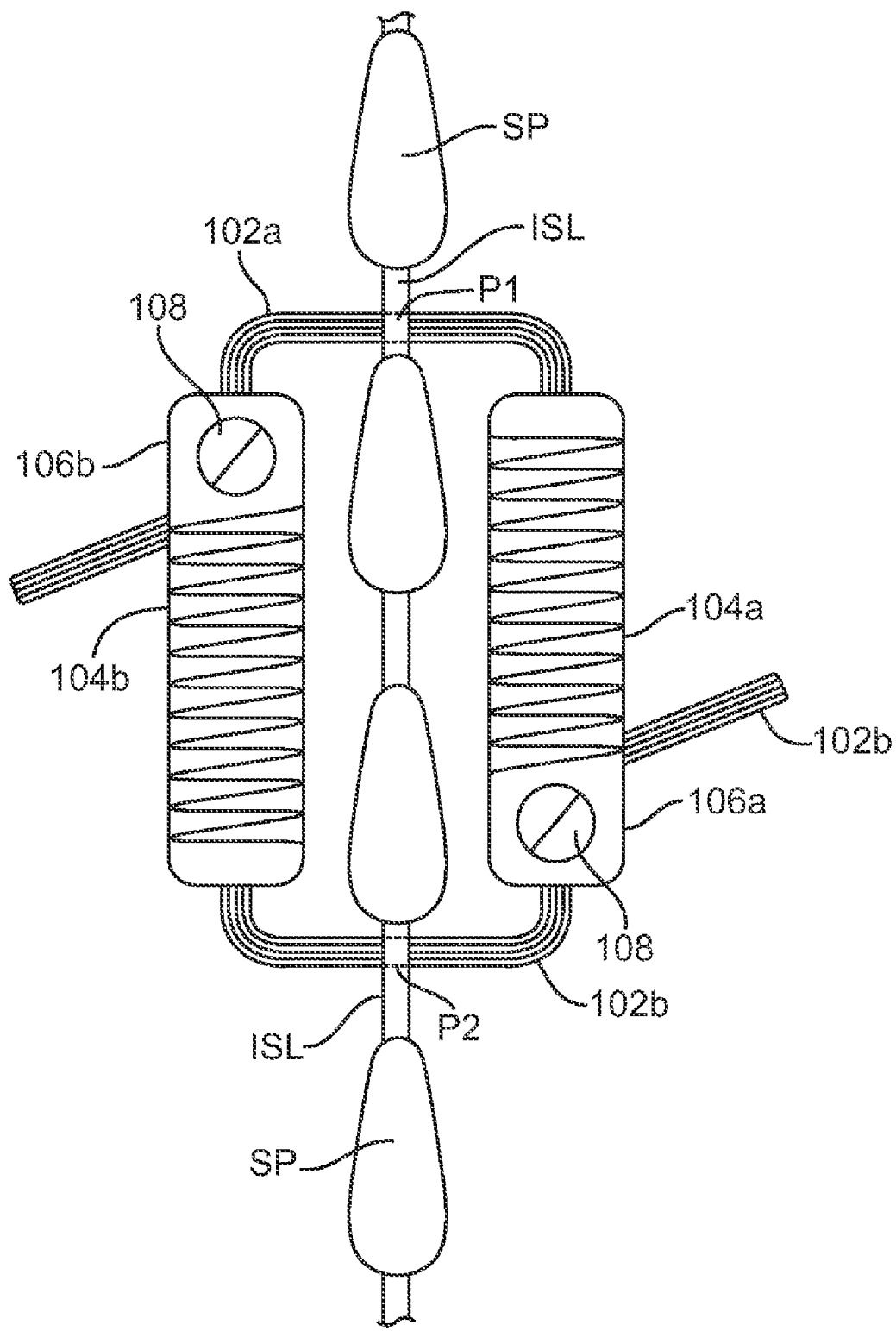

The free ends of each tether 702a and 702b may then be coupled with the compliance member of the opposite tether to form a closed loop spinous process constraint device as seen in FIG. 15K. Excess material from the tether ends may be severed or left in place. The tension and/or circumference in the spinous process constraint device may then be adjusted as required. Further disclosure on adjusting the tether is disclosed in U.S. patent application Ser. No. 12/106,049, the entire contents of which are incorporated herein by reference.

Figure 23:
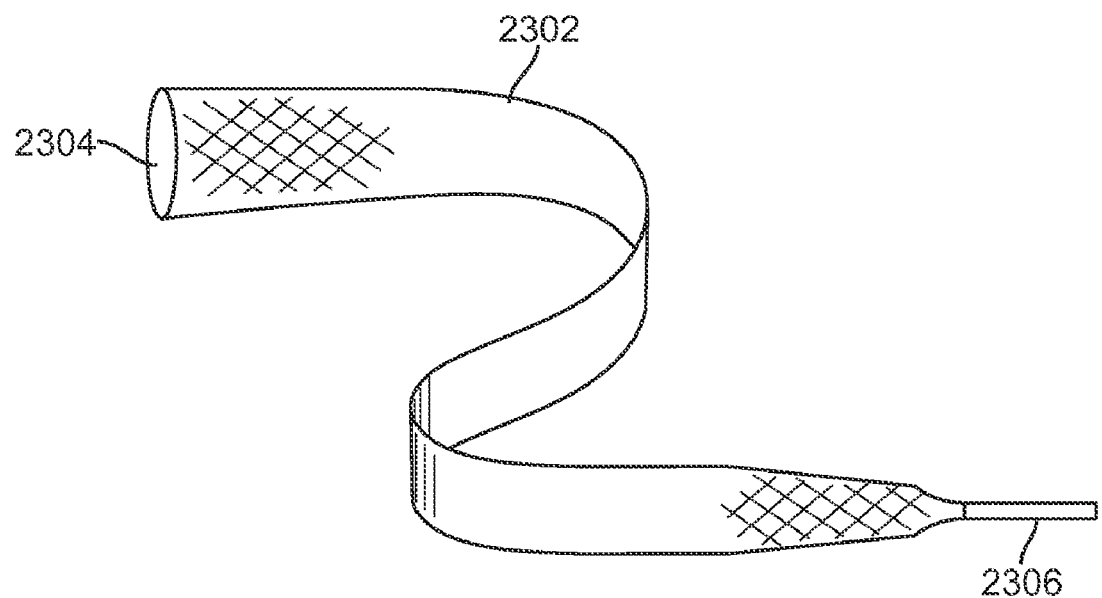
FIG. 23 illustrates another embodiment of a leader.
Figure 24:
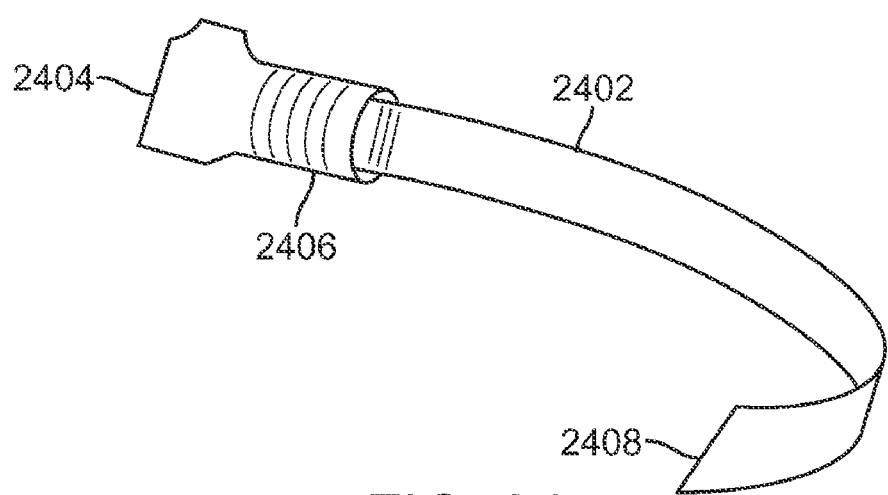
FIG. 24 illustrates a portion of a constraint device.
Figure 25A:
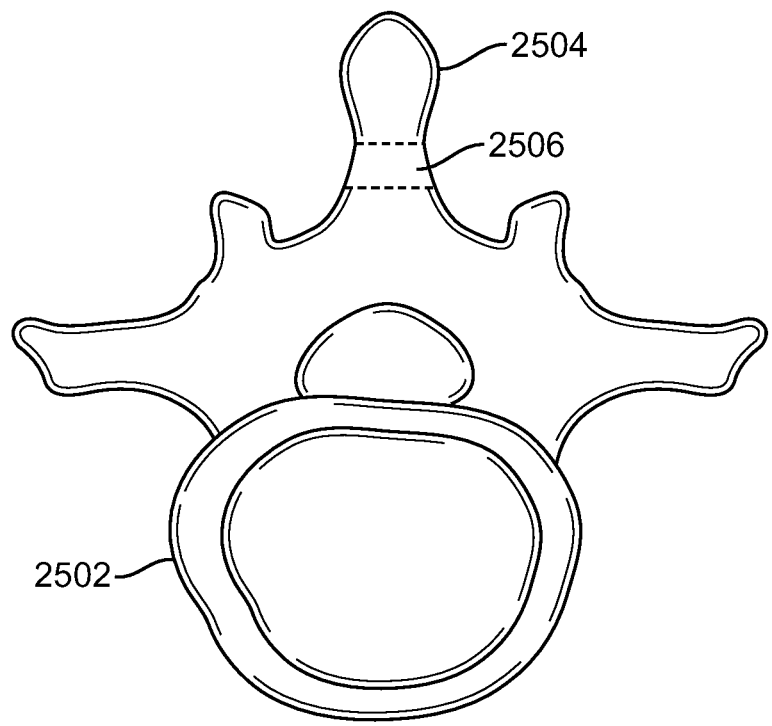
FIGS. 25A-25B illustrate a hole drilled in a spinous process of a vertebra.
Figure 25B:
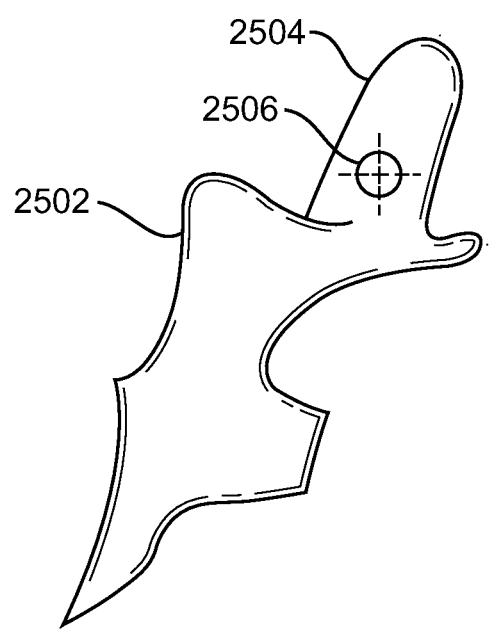

FIG. 23 illustrates another exemplary embodiment of a leader that may be used to facilitate introduction of a constraint device through tissue. A hollow textile woven tube 2302 is fabricated from a polymer such as ultra high molecular weight polyethylene or other flexible polymers and has a central channel 2304 running through the tube. One end of the tube includes a hard, reduced diameter tip 2306 that serves as a leading edge for introduction through tissue. This may be formed by crimping a metal tip over the textile tube, melting the tip with heat, coating the tip with another polymer, overmolding a tip, or other techniques known in the art. The opposite end is open and has an aperture for receiving a portion of the constraint device 2402, such as the one illustrated in FIG. 24 which includes a flexible strap 2402, a free end 2408, a compliance member 2406 and a receiver 2404 for receiving the opposite end of another constraint device. Device 2402 is one half of a constraint device which includes another strap, compliance member and receiver. Both halves together generally take the same form as the constraint device illustrated in FIG. 2. The leader may be used to help advance a constraint device through the interspinous ligament or through other tissue, such as a small hole in a spinous process or through the sacrum. FIG. 25A illustrates an axial view of a vertebra 2502 having a spinous process 2504 with a hole 2506 drilled therethrough. FIG. 25B illustrates a sideview of vertebra 2502.

Figure 26A:
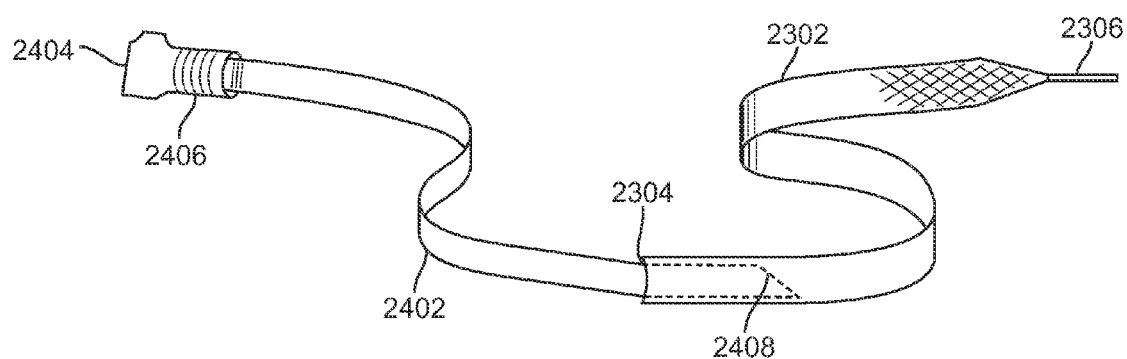
FIGS. 26A-26F illustrate use of the leader in FIG. 23.
Figure 26B:
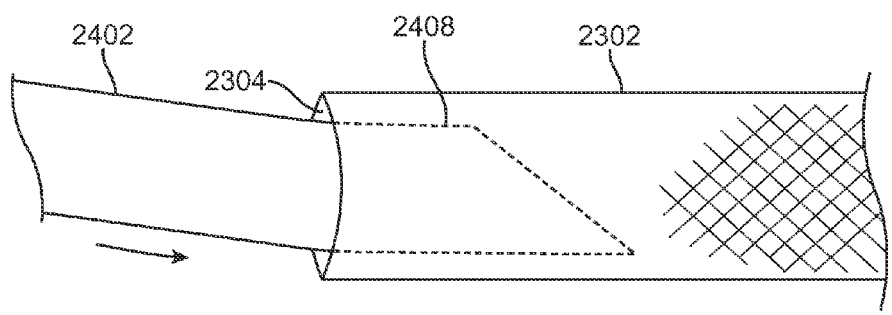
Figure 26C:
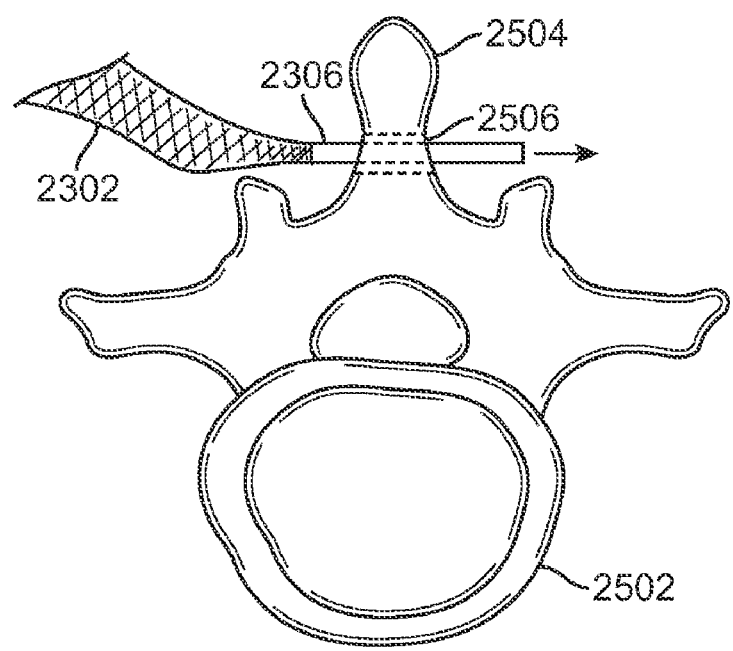
Figure 26D:
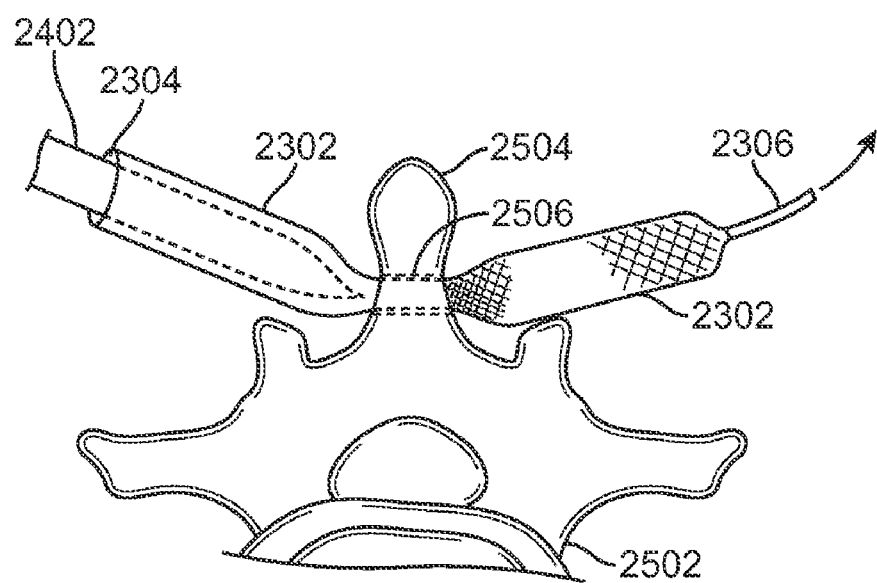
Figure 26E:
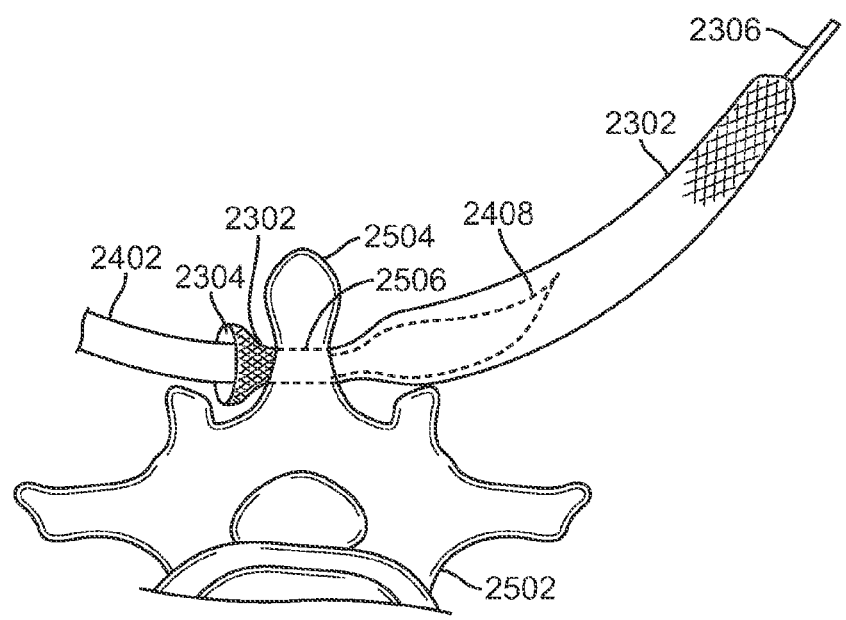
Figure 26F:
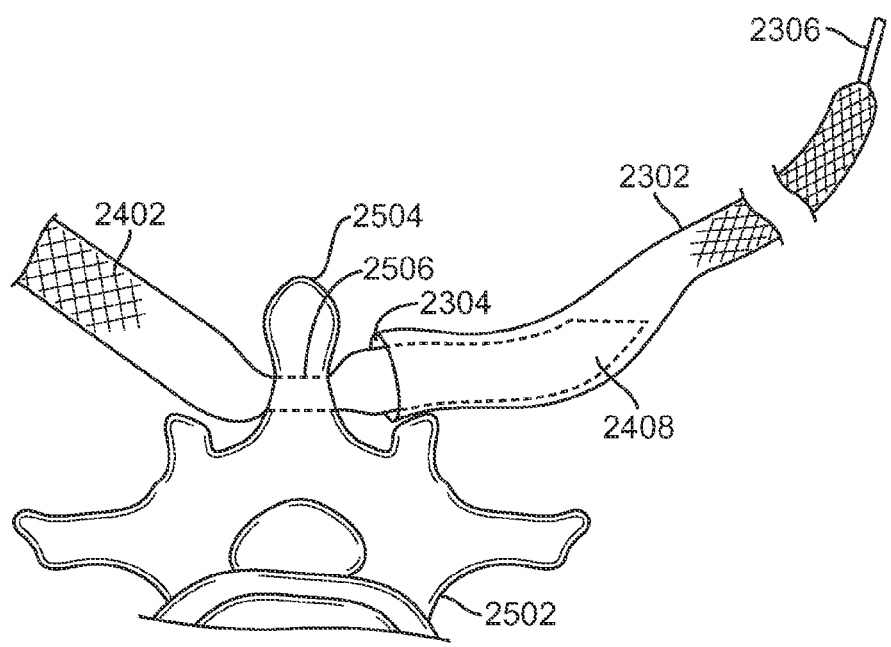

In use, the central channel 2304 is opened up by inserting a mandrel into the channel and then the free end 2408 of the constraint device 2402 is advanced into the channel 2304. FIG. 26A illustrates the constraint device 2402 inserted into the polyethylene woven textile tube 2302 and FIG. 26B is a close up view showing the free end 2408 inserted into the channel 2304 of the textile tube 2302. The constraint device 2402 may take the form of any of the constraint devices disclosed herein or incorporated by reference. Additionally, the constraint device may be inserted partially or all the way into the textile tube. An adequate length of the constraint device is preferably inserted into the textile tube so that once the constraint device has passed through the hole in the spinous process (or interspinous ligament) and the textile tube removed, a sufficient length of the constraint device emerges from the hole and may be located and grasped. The tip 2306 of tube of the tube 2302 is then advanced through a hole 2506 drilled in spinous process 2504 of vertebra 2502 as illustrated in FIG. 26C. The tube 2302 may be pinched by the surgeon's fingers or clamped to keep the strap 2402 in the channel 2302 as the tip 2306 is advanced through the hole 2506. As the portion of the textile tube holding the strap enters the hole 2506, as seen in FIG. 26D, the tube is forced to collapse around the strap 2302 and the resulting friction between the two components helps the tube retain the strap is both are advanced through the hole. A surgeon may use his hands or another tool to help pull the tip 2306 through the hole in the spinous process. Hands may be preferable, at least initially so that tactile feedback may be used to help locate the tip which is hard and clearly distinguishable from the surrounding tissue. The tip 2306 is long enough so that it may pass through the hole in a spinous process (or the interspinous ligament) and still have enough of the tip remaining on either side of the bone that may be grasped and pushed or pulled through the ligament or bone. FIG. 26E illustrates advancement of the leading edge 2408 of the constraint device through the hole 2506 in the spinous process 2504 and FIG. 26F illustrates the textile tube 2302 advanced completely through the hole 2506. The textile tube 2302 is then easily disengaged from the strap 2402 of the constraint device. Because the hole no longer constraints the textile tube against the strap, the two will release from one another simply by pulling them apart. The process may be repeated again for attachment to a hole in another spinous process or a hole in a crest of the sacrum. The same apparatus may also be used to pass the strap through the interspinous ligaments and other tissue disposed between adjacent spinous processes.

Figure 28:
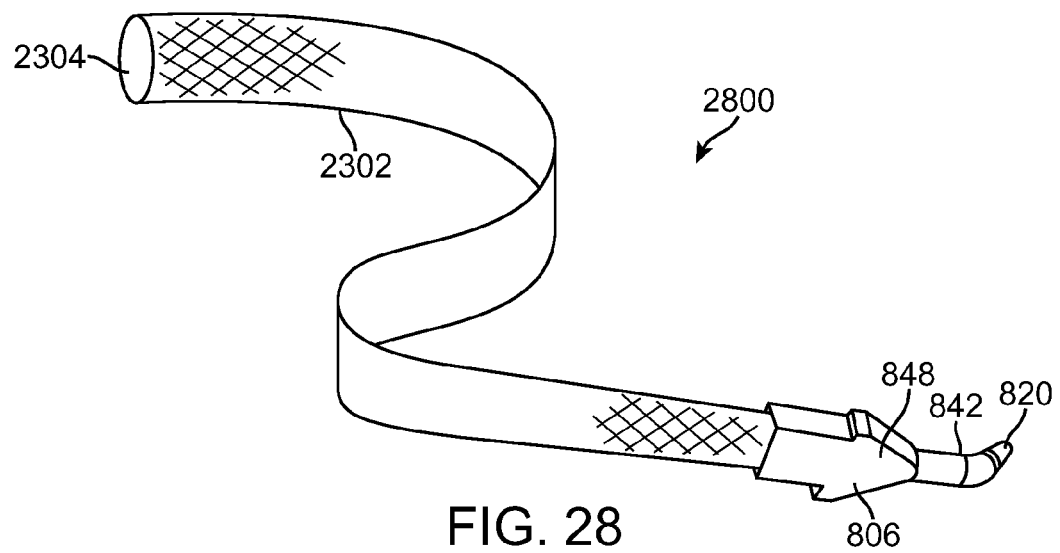
FIG. 28 illustrates another exemplary embodiment of a leader.

FIG. 28 illustrates another exemplary embodiment of a leader. This embodiment combines the piercing element 806 of FIG. 22 with the textile tube 2302 of FIG. 23. The piercing tip 806 includes a main body 848, a sharp tip 820 for piercing an interspinous ligament and having a curved portion 842 that will preferentially pierce the ligament in one direction, here clockwise. The piercing tip also includes a tapered shoulder that facilitates expansion of the pierced hole as the tip is passed through the tissue. The piercing tip 806 generally takes the same form as previously described with respect to FIG. 22. The textile tube 2302 has an open end 2304 for receiving the surgical strap or tether and generally takes the same form as previously described with respect to FIG. 23. Use of this device generally takes the same form as described for the piercing tip and the textile tube, both previously described.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A surgical method for deploying an implant, said method comprising:
   piercing tissue with a leader coupled to a tool shaft, wherein the tissue comprises an interspinous ligament disposed between adjacent spinous processes;
   actuating an actuator on the tool shaft to release the leader from the shaft;
   advancing the leader and implant through the tissue, wherein the implant is releasably coupled with the leader;
   releasing the leader from the implant; and
   removing the leader from a patient's body, the implant remaining therein.

2. A method as in claim 1, wherein the implant comprises a spinous process constraint.

3. A method as in claim 1, wherein piercing comprises orienting the leader relative to the tissue using an indicator on the tool shaft.

4. A method as in claim 1, wherein piercing creates an initial puncture, the method further comprising distending the tissue to enlarge the puncture.

5. A method as in claim 1, wherein actuating the actuator comprises rotating a knob.

6. A method as in claim 1, wherein an inner shaft is disposed at least partially in the tool shaft and actuating the actuator comprises linearly moving the tool shaft relative to the inner shaft.

7. A method as in claim 1, wherein releasing the leader comprises actuating an actuator on the tool shaft.

8. A method as in claim 1, wherein an inner shaft is disposed at least partially in the tool shaft and releasing the leader comprises aligning an aperture in the inner shaft with an aperture in the tool shaft.

9. A method as in claim 1, wherein releasing the leader comprises slidably disengaging the leader from the tool shaft.

10. A method as in claim 1, wherein an inner shaft is disposed at least partially in the tool shaft and releasing the leader comprises linearly moving the tool shaft relative to the inner shaft.

11. A method as in claim 1, wherein releasing the leader from the implant comprises the step of severing.

12. A method as in claim 1, further comprising coupling the leader with the implant.

13. A method as in claim 12, wherein coupling the leader comprises closing a lasso around the implant.

14. A method as in claim 12, wherein the leader comprises a loop and coupling the leader comprises advancing a collar over the loop so as to capture the implant with the loop.

15. A method as in claim 12, wherein coupling the leader comprises hooking the implant with a loop.

16. A method as in claim 1, wherein the leader comprises a filament and advancing the leader comprises pulling the filament through the tissue.

17. A method as in claim 1, wherein advancing the leader comprises capturing the leader with a capture tool.

18. A method as in claim 17, wherein capturing the leader comprises covering the leader with a guard to prevent exposure of sharp portions therefrom.

19. A method as in claim 1, further comprising releasably locking the leader with the tool shaft.

20. A method as in claim 19, wherein releasably locking comprises actuating an actuator mechanism on the tool shaft.

21. A method as in claim 1, further comprising tactilely distinguishing the leader from the tissue or adjacent tissue.

22. A method as in claim 1, wherein the leader is shaped to pass the leader through the tissue preferentially in one direction.

23. A method as in claim 1, wherein the step of advancing the leader and implant through the tissue comprises: folding the implant around a portion of the leader such that a folded portion of the implant forms a leading edge; and advancing the leading edge through the tissue, whereby a free end of the implant trails the leading edge and is protected from damage as the implant is passed through the tissue.

24. A method as in claim 1, further comprising: observing radiopaque markers on the implant with a fluoroscope; and verifying correct position of the implant in the patient.

25. A surgical method for deploying an implant, said method comprising:
piercing tissue with a leader coupled to a tool shaft, wherein the leader comprises a filament;
actuating an actuator on the tool shaft to release the leader from the shaft;
advancing the leader and implant through the tissue, wherein the implant is releasably coupled with the leader, and wherein advancing the leader comprises pulling the filament through the tissue;
releasing the leader from the implant; and
removing the leader from a patient's body, the implant remaining therein.

26. A method as in claim 25, wherein the implant comprises a spinous process constraint.

27. A method as in claim 25, wherein the tissue comprises an interspinous ligament disposed between adjacent spinous processes.

28. A method as in claim 25, wherein piercing comprises orienting the leader relative to the tissue using an indicator on the tool shaft.

29. A method as in claim 25, wherein piercing creates an initial puncture, the method further comprising distending the tissue to enlarge the puncture.

30. A method as in claim 25, wherein actuating the actuator comprises rotating a knob.

31. A method as in claim 25, wherein an inner shaft is disposed at least partially in the tool shaft and actuating the actuator comprises linearly moving the tool shaft relative to the inner shaft.

32. A method as in claim 25, wherein releasing the leader comprises actuating an actuator on the tool shaft.

33. A method as in claim 25, wherein an inner shaft is disposed at least partially in the tool shaft and releasing the leader comprises aligning an aperture in the inner shaft with an aperture in the tool shaft.

34. A method as in claim 25, wherein releasing the leader comprises slidably disengaging the leader from the tool shaft.

35. A method as in claim 25, wherein an inner shaft is disposed at least partially in the tool shaft and releasing the leader comprises linearly moving the tool shaft relative to the inner shaft.

36. A method as in claim 25, wherein releasing the leader from the implant comprises the step of severing.

37. A method as in claim 25, further comprising coupling the leader with the implant.

38. A method as in claim 37, wherein coupling the leader comprises closing a lasso around the implant.

39. A method as in claim 37, wherein the leader comprises a loop and coupling the leader comprises advancing a collar over the loop so as to capture the implant with the loop.

40. A method as in claim 37, wherein coupling the leader comprises hooking the implant with a loop.

41. A method as in claim 25, wherein advancing the leader comprises capturing the leader with a capture tool.

42. A method as in claim 41, wherein capturing the leader comprises covering the leader with a guard to prevent exposure of sharp portions therefrom.

43. A method as in claim 25, further comprising releasably locking the leader with the tool.

44. A method as in claim 25, wherein releasably locking comprises actuating an actuator mechanism on the tool.

45. A method as in claim 25, further comprising tactilely distinguishing the leader from the tissue or adjacent tissue.

46. A method as in claim 25, wherein the leader is shaped to pass the leader through the tissue preferentially in one direction.

47. A method as in claim 25, wherein the step of advancing the leader and implant through the tissue comprises:
folding the implant around a portion of the leader such that a folded portion of the implant forms a leading edge; and
advancing the leading edge through the tissue, whereby a free end of the implant trails the leading edge and is protected from damage as the implant is passed through the tissue.

48. A method as in claim 25, further comprising:
observing radiopaque markers on the implant with a fluoroscope; and
verifying correct position of the implant in the patient.

49. A surgical method for deploying an implant, said method comprising:
piercing tissue with a leader coupled to a tool shaft, wherein an inner shaft is disposed at least partially in the tool shaft;
actuating an actuator on the tool shaft to release the leader from the shaft;
advancing the leader and implant through the tissue, wherein the implant is releasably coupled with the leader;
releasing the leader from the implant, wherein releasing the leader comprises aligning an aperture in the inner shaft with an aperture in the tool shaft; and removing the leader from a patient's body, the implant remaining therein.

50. A method as in claim 49, wherein the implant comprises a spinous process constraint.

51. A method as in claim 49, wherein the tissue comprises an interspinous ligament disposed between adjacent spinous processes.

52. A method as in claim 49, wherein piercing comprises orienting the leader relative to the tissue using an indicator on the tool shaft.

53. A method as in claim 49, wherein piercing creates an initial puncture, the method further comprising distending the tissue to enlarge the puncture.

54. A method as in claim 49, wherein actuating the actuator comprises rotating a knob.

55. A method as in claim 49, wherein an inner shaft is disposed at least partially in the tool shaft and actuating the actuator comprises linearly moving the tool shaft relative to the inner shaft.

56. A method as in claim 49, wherein releasing the leader comprises actuating an actuator on the tool shaft.

57. A method as in claim 49, wherein releasing the leader comprises slidably disengaging the leader from the tool shaft.

58. A method as in claim 49, wherein an inner shaft is disposed at least partially in the tool shaft and releasing the leader comprises linearly moving the tool shaft relative to the inner shaft.

59. A method as in claim 49, wherein releasing the leader from the implant comprises the step of severing.

60. A method as in claim 49, further comprising coupling the leader with the implant.

61. A method as in claim 60, wherein coupling the leader comprises closing a lasso around the implant.

62. A method as in claim 60, wherein the leader comprises a loop and coupling the leader comprises advancing a collar over the loop so as to capture the implant with the loop.

63. A method as in claim 60, wherein coupling the leader comprises hooking the implant with a loop.

64. A method as in claim 60, wherein the leader comprises a filament and advancing the leader comprises pulling the filament through the tissue.

65. A method as in claim 60, wherein advancing the leader comprises capturing the leader with a capture tool.

66. A method as in claim 65, wherein capturing the leader comprises covering the leader with a guard to prevent exposure of sharp portions therefrom.

67. A method as in claim 49, further comprising releasably locking the leader with the tool shaft.

68. A method as in claim 67, wherein releasably locking comprises actuating an actuator mechanism on the tool shaft.

69. A method as in claim 49, further comprising tactilely distinguishing the leader from the tissue or adjacent tissue.

70. A method as in claim 49, wherein the leader is shaped to pass the leader through the tissue preferentially in one direction.

71. A method as in claim 49, wherein the step of advancing the leader and implant through the tissue comprises:
    folding the implant around a portion of the leader such that a folded portion of the implant forms a leading edge; and
    advancing the leading edge through the tissue, whereby a free end of the implant trails the leading edge and is protected from damage as the implant is passed through the tissue.

72. A method as in claim 49, further comprising:
    observing radiopaque markers on the implant with a fluoroscope; and verifying correct position of the implant in the patient.

73. A surgical method for deploying an implant, said method comprising:
    coupling a leader with the implant, wherein coupling the leader comprises closing a lasso around the implant;
    piercing tissue with a leader coupled to a tool shaft;
    actuating an actuator on the tool shaft to release the leader from the shaft;
    advancing the leader and implant through the tissue, wherein the implant is releasably coupled with the leader;
    releasing the leader from the implant; and
    removing the leader from a patient's body, the implant remaining therein.

74. A method as in claim 73, wherein the implant comprises a spinous process constraint.

75. A method as in claim 73, wherein the tissue comprises an interspinous ligament disposed between adjacent spinous processes.

76. A method as in claim 73, wherein piercing comprises orienting the leader relative to the tissue using an indicator on the tool shaft.

77. A method as in claim 73, wherein piercing creates an initial puncture, the method further comprising distending the tissue to enlarge the puncture.

78. A method as in claim 73, wherein actuating the actuator comprises rotating a knob.

79. A method as in claim 73, wherein an inner shaft is disposed at least partially in the tool shaft and actuating the actuator comprises linearly moving the tool shaft relative to the inner shaft.

80. A method as in claim 73, wherein releasing the leader comprises actuating an actuator on the tool shaft.

81. A method as in claim 73, wherein an inner shaft is disposed at least partially in the tool shaft and releasing the leader comprises aligning an aperture in the inner shaft with an aperture in the tool shaft.

82. A method as in claim 73, wherein releasing the leader comprises slidably disengaging the leader from the tool shaft.

83. A method as in claim 73, wherein an inner shaft is disposed at least partially in the tool shaft and releasing the leader comprises linearly moving the tool shaft relative to the inner shaft.

84. A method as in claim 73, wherein releasing the leader from the implant comprises the step of severing.

85. A method as in claim 73, wherein the leader comprises a loop and coupling the leader comprises advancing a collar over the loop so as to capture the implant with the loop.

86. A method as in claim 73, wherein coupling the leader comprises hooking the implant with a loop.

87. A method as in claim 73, wherein the leader comprises a filament and advancing the leader comprises pulling the filament through the tissue.

88. A method as in claim 73, wherein advancing the leader comprises capturing the leader with a capture tool.

89. A method as in claim 88, wherein capturing the leader comprises covering the leader with a guard to prevent exposure of sharp portions therefrom.

90. A method as in claim 73, further comprising releasably locking the leader with the tool shaft.

91. A method as in claim 73, wherein releasably locking comprises actuating an actuator mechanism on the tool shaft.

92. A method as in claim 73, further comprising tactilely distinguishing the leader from the tissue or adjacent tissue.

93. A method as in claim 73, wherein the leader is shaped to pass the leader through the tissue preferentially in one direction.

94. A method as in claim 73, wherein the step of advancing the leader and implant through the tissue comprises:
folding the implant around a portion of the leader such that a folded portion of the implant forms a leading edge; and
advancing the leading edge through the tissue, whereby a free end of the implant trails the leading edge and is protected from damage as the implant is passed through the tissue.

95. A method as in claim 73, further comprising:
observing radiopaque markers on the implant with a fluoroscope; and
verifying correct position of the implant in the patient.

\* \* \* \* \*